United States Patent
Leblanc et al.

(10) Patent No.: US 6,365,592 B1
(45) Date of Patent: Apr. 2, 2002

(54) PHOSPHONIC AND CARBOXYLIC ACID DERIVATIVES AS INHIBITORS OF PROTEIN TYROSINE PHOSPHATASE-1B (PTP-1B)

(75) Inventors: Yves Leblanc, Kirkland; Claude Dufresne; Patrick Roy, both of Dollard des Ormeaux; Zhaoyin Wang, Kirkland, all of (CA)

(73) Assignee: Merck Frosst Canada & Co., Quebec (CA)

( * ) Notice: Subject to any disclaimer, the term of this patent is extended or adjusted under 35 U.S.C. 154(b) by 0 days.

(21) Appl. No.: 09/570,092

(22) Filed: May 12, 2000

Related U.S. Application Data

(60) Provisional application No. 60/134,150, filed on May 14, 1999, and provisional application No. 60/158,778, filed on Oct. 12, 1999.

(51) Int. Cl.$^7$ .................. A01N 57/00; A61K 31/505; C01B 25/16; C07F 9/02; C07F 9/547

(52) U.S. Cl. .................. 514/255.01; 514/75; 514/274; 514/311; 514/317; 514/359; 514/423; 514/456; 423/316; 544/243; 544/315; 544/337; 544/386; 546/22; 546/152; 546/192; 548/413; 549/218

(58) Field of Search ................. 514/75, 255.01, 514/274, 311, 317, 359, 423, 456; 423/316; 544/243, 315, 337, 386; 546/22, 152, 192; 548/413; 549/218

(56) References Cited

U.S. PATENT DOCUMENTS 6,066,715 A * 5/2000 Desmarais et al. .......... 530/331

FOREIGN PATENT DOCUMENTS

| WO | WO97/40017 | 10/1997 |
|----|------------|---------|
| WO | WO 98/20156 | 5/1998 |
| WO | WO 00/17211 | 3/2000 |

OTHER PUBLICATIONS

Ahmad, et al. J. Biol. Chem. 270:20503–20508, 1995.
Bin, et al., Tetrahedron, NL, Elsevier Science Publishers, Amsterdam, vol. 52, No. 30, pp. 9963–9970.
Caplan, et al, Bioorganic & Medicinal Chem. Letters, GB, Oxford, vol. 8, No. 5, pp. 515–520.
Charbonneau, et al, Proc. Natl. Acad, Sci. USA 86: 5252–5256, 1989.
Fischer, et al., Science 253: 401–406, 1991.
Goldstein, Receptor 3:1–15, 1993.
Kotoris, et al., J. Org. Chem. 63, 8052–8057, 1998.
Kotoris, et al., Bioorg. Med. Chem. vol. 8, pp. 3275–3280, 1998.
Seely, et al., Diabetes 45: 1379–1385, 1996.
Taylor, et al., Bioorg. Med. Chem., vol. 6(9), pp. 1457–1468, 1998.
Taylor, et al., Bioorg. Med. Chem., vol. 6, p. 2235, 1998.
Taylor, et al., Tetrahedron Letters, vol. 8, No. 45, pp. 8089–8092, 1996.
Taylor, et al., Tetrahedron, No. 54, pp. 1691–1714, 1998.
Wang, et al., Bioorg. Med. Chem., Let. 8(4) 345–350, 1998.
White, et al., J. Biol. Chem. 269: 11–4, 1994.
Yokomatsu, et al., Tetrahedron, NL, Elsevier Science Publishers, Amsterdam, vol. 54, No. 32, pp. 9341–9356.
Burke, et al., Bioorg. Med. Chem. Letters, vol. 9, pp. 347–352, 1999.
Yao, et al., Tetrahedron, vol. 55, pp. 2865–2874, 1999.
Beaulieu, et al.., J. Med. Chem., vol. 42, pp. 1757–1766, 1999.

* cited by examiner

Primary Examiner—Mukund J. Shah
Assistant Examiner—Tamthom N. Truong
(74) Attorney, Agent, or Firm—James L. McGinnis; David L. Rose

(57) ABSTRACT

The invention encompasses compounds represented by formula I:

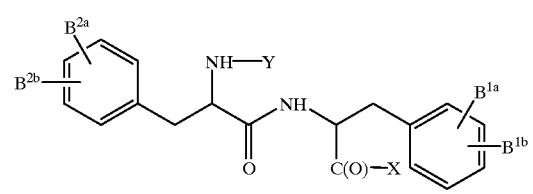

as well as compositions and methods of treatment. The compounds are inhibitors of the PTP-1B enzyme.

15 Claims, No Drawings

PHOSPHONIC AND CARBOXYLIC ACID DERIVATIVES AS INHIBITORS OF PROTEIN TYROSINE PHOSPHATASE-1B (PTP-1B)

This application is based on and claims priority from, US Provisional Application Nos. 60/134,150, filed May 14, 1999, and 60/158,778, filed Oct. 12, 1999, which are incorporated herein in their entirety.

BACKGROUND OF THE INVENTION

This invention relates to a novel class of phosphonic and carboxylic acid derivatives that are useful as inhibitors of PTP-1B.

Protein tyrosine phosphatases (PTPases) are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15). Lilce other PTPases, PTP-1B has a catalytic domain containing arginine and cysteine residues that are critical to the enzyme's activity (Streuli et al., 1990, EMBO J. 9:2399–2407, Guan et al., 1990, Proc. Natl. Acad. Sci. USA 87:1501–1505; Guan & Dixon, 1991, J. Biol. Chem. 266:17026–17030). The amino terminal 35 amino acid residues of PTP-1B localizes the protein to the endoplasmic reticulum (Frangioni et al., 1992, Cell 68:545–560).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45: 1379–1385 (Seely) studied the relationship of PTP-1B and the insulin receptor iii vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995. J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Inhibitors of PTP-1B improve insulin-sensitivity and thus have utility in preventing or treating Type 1 and Type 2 diabetes, improving glucose tolerance, improving insulin-sensitivity when there is insulin-resistance and treating or preventing obesity. In addition, the compounds are useful for treating or preventing cancer, neurodegenerative diseases and the like.

SUMMARY OF THE INVENTION

The present invention relates to a compound represented by formula I:

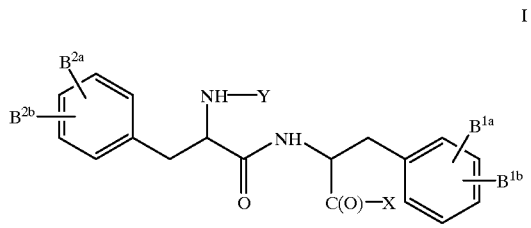

I or a pharmaceutically acceptable salt or hydrate thereof wherein:

one of $B^{1a}$, $B^{1b}$, $B^{2a}$ and $B^{2b}$ represents $CF_2$—$PO_3H_2$ or $CF_2$—$CO_2H$, one of $B^{1a}$, $B^{1b}$, $B^{2a}$ and $B^{2b}$ represents H, and the others are selected from the group consisting of: $R^4$, OH, halo, $CHF_2$, $CF_3$, CHF—$CO_2H$, $CF_2$—$CO_2H$, $CF_2$—$C(R^5)(R^6)OH$, CHF—$PO_3H_2$, $CH_2$—$PO_3H_2$, $C(R^5)(R^6)OH$, $S(O)yR^5$, wherein y is 0, 1 or 2, $S(O)_2NR^5$ $R^6$, $CFHSO_3H$, $CF_2SO_3H$, $CFHS(O)_2NR^5R^6$, $CF_2S(O)_2NR^5R^6$, $NR^6S(O)_2R^5$, CFH-Hetcy, $CF_2$-Hetcy, $CH_2S(O)_2$-Hetcy, $CFHS(O)_2$-Hetcy, $CF_2S(O)_2$-Hetcy, $CH_2S$-Hetcy, CFHS-Hetcy, $CF_2S$-Hetcy, $OC(R^5)(R^6)F$, $C(R^5)(R^6)F$, O—$CF_2CO_2R^4$, O-$CH_2CO_2R^4$, $C(R^5)(R^6)CO_2R^4$, $CO_2R^4$, CFH-aryl, $CF_2$-aryl, $CH_2S(O)_2$-aryl, CFHS(O)$_2$-aryl, $CF_2S(O)_2$-aryl, $CH_2S$-aryl, CFHS-aryl and $CF_2S$-aryl, such that when one of $B^{1a}$ and $B^{1b}$ represents $CF_2$—$CO_2H$, at least one of $B^{2a}$ and $B^{2b}$ represents $CF_2$—$PO_3H_2$ or $CF_2$—$CO_2H$, and when one of $B^{2a}$ and $B^{2b}$ represents $CF_2$—$CO_2H$, at least one of $B^{1a}$ and $B^{1b}$ represents $CF_2$—$PO_3H_2$ or $CF_2$—$CO_2H$;

Hetcy is selected from the group consisting of:
(a) a 5–15 membered heteroaryl group containing 1–4 heteroatoms selected from O, S(O)y and N, wherein y is as defined above, and 0–2 carbonyl groups, optionally substituted with 1–4 members selected from $R^a$; and
(b) a non-aromatic carbocyclic structure containing 5–15 carbon atoms, interrupted by 1–4 heteroatoms selected from O, S(O)y wherein y is as previously defined, and N, and optionally containing 1–2 carbonyl groups, and optionally substituted with 1–4 members selected from $R^a$;

aryl is a 6–10 membered aromatic ring system that is optionally substituted with 1–4 members selected from $R^a$;

each $R^a$ is independently selected from the group consisting of: halo, $NO_2$, $N_3$, OH, CN, $C(O)NH_2$, $C(O)NHC_{1-3}$alkyl, $C(O)N(C_{1-3}$alkyl)$_2$, $CO_2H$, $CO_2$—$C_{1-10}$alkyl, $C_{1-10}$alkyl, $C_{1-10}$haloalkyl, $C_{1-10}$haloalkoxy, $C_{1-10}$alkoxy, $C_{1-10}$alkylthio, $C_{1-10}$alkylsulfinyl, $C_{1-10}$alkylsulfonyl, phenylsulfonyl and phenyl;

X is OH or $NH_2$.

Y is selected from the group consisting of: H, $C_{1-6}$alkyl, $R^1ZCO$—, $R^2$— and $R^3S(O)_2$—;

Z represents a bond or is selected from O, S(O)yCH$_2$, NR$^4$ or CH=CH;

R$^4$ represents H, C$_{1-6}$alkyl, Hetcy or aryl, said alkyl, Hetcy and aryl being optionally substituted with 1–3 members selected from R$^a$;

R$^1$ is selected from the group consisting of:
(a) C$_{1-10}$alkyl,
(b) C$_{1-6}$fluoroalkyl, optionally substituted with a hydroxy group;
(c) aryl optionally substituted with 1–3 substituents selected from R$^a$;
(d) heteroaryl, said heteroaryl group being a monocyclic aromatic ring of 5 atoms, said ring having one heteroatom which is O, S or N, and optionally 1, 2, or 3 additional N atoms; or a monocyclic ring of 6 atoms, said ring having one heteroatom which is O, S or N, and optionally 1, 2, or 3 additional N atoms, said heteroaryl group being optionally substituted with from 1–3 substituents selected from R$^a$;
(e) benzoheterocycle in which the heterocycle is a 5, 6, or 7-membered ring containing 1 or 2 heteroatoms selected from O, S and N, optionally containing a carbonyl, sulfinyl or sulfonyl group; said benzoheterocycle being optionally substituted with 1–3 substituents selected from R$^a$;
(f) a heterocycloalkyl group of 5, 6 or 7 members which contains 1 or 2 heteroatoms selected from O, S and N, and optionally containing a carbonyl group or a sulfonyl group;
(g) a benzocarbocycle in which the carbocycle is a 5, 6, or 7-membered ring which optionally contains a carbonyl group, optionally substituted with 1–2 substituents selected from R$^a$;
(h) a bicyclic heteroaryl group having 8, 9 or 10 members, containing 1 to 5 heteroatoms selected from O, S and N, optionally substituted with 1–2 substituents selected from Ra; and
(i) hydrogen;

R$^2$ is the acyl residue of an amino acid, the amino group of which may be optionally substituted by an acyl group of the structure R$^1$ZCO— or C$_{1-6}$ alkyl, and in the case of a dicarboxylic amino acid, the terminal carboxyl may optionally be in the form of a C$_{1-4}$ alkyl ester;

R$^3$ is selected from the group consisting of:
(a) C$_{1-10}$alkyl,
(b) C$_{1-6}$fluoroalkyl, and
(c) C$_{6-10}$aryl optionally substituted as defined above, and R$^5$ and R$^6$ independently represent members selected from the group consisting of: H, C$_{1-10}$alkyl, C$_{2-10}$alkenyl, aryl, Hetcy, CONH$_2$, CO$_2$H, CO$_2$—R$^4$, C(O)R$^4$, C$_{1-6}$fluoroalkyl, said alkyl aryl, and Hetcy groups being optionally substituted with 1–3 substituents selected from R$^a$;

or R$^5$ and R$^6$ are taken in combination and represent a 7 membered carbocyclic ring, optionally interrupted with 1–3 heteroatoms selected from O, S(O)y and N, and optionally substituted with 1–3 members selected from R$^a$.

The invention also encompasses pharmaceutical compositions and methods of treatment.

DETAILED DESCRIPTION OF THE INVENTION

One aspect of the present invention relates to compounds represented by formula I:

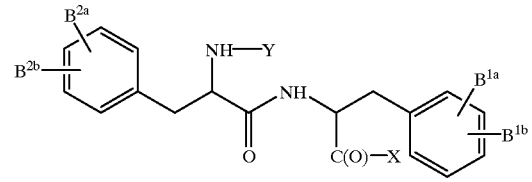

as well as pharmaceutically acceptable salts and hydrates thereof wherein:

one of B$^{1a}$, B$^{1b}$, B$^{2a}$ and B$^{2b}$ represents CF$_2$—PO$_3$H$_2$ or CF$_2$—CO$_2$H, one of B$^{1a}$, B$^{1b}$, B$^{2a}$ and B$^{2b}$ represents H, and the others are selected from the group consisting of: R$^4$, OH, halo, CHF$_2$, CF$_3$, CHF—CO$_2$H, CF$_2$—CO$_2$H, CF$_2$—C(R$^5$)(R$^6$)OH, CHF—PO$_3$H$_2$, CH$_2$—PO$_3$H$_2$, C(R$^5$)(R$^6$)OH, S(O)yR$^5$, wherein y is 0, 1 or 2, S(O)$_2$NR$^5$R$^6$, CFHSO$_3$H, CF$_2$SO$_3$H, CFHS(O)$_2$NR$^5$R$^6$, CF$_2$S(O)$_2$NR$^5$R$^6$, NR$^6$S(O)$_2$R$^5$, CFH-Hetcy, CF$_2$-Hetcy, CH$_2$S(O)$_2$-Hetcy, CFHS(O)$_2$-Hetcy, CF$_2$S(O)$_2$-Hetcy, CH$_2$S-Hetcy, CFHS-Hetcy, CF$_2$S-Hetcy, OC(R$^5$)(R$^6$)F, C(R$^5$)(R$^6$)F, O-CF$_2$CO$_2$R$^4$, O—CH$_2$CO$_2$R$^4$, C(R$^5$)(R$^6$)CO$_2$R$^4$, CO$_2$R$^4$, CFH-aryl, CF$_2$-aryl, CH$_2$S(O)$_2$-aryl, CFHS(O)$_2$-aryl, CF$_2$S(O)$_2$-aryl, CH$_2$S-aryl, CFHS-aryl and CF$_2$S-aryl;

such that when one of B$^{1a}$ and B$^{1b}$ represents CF$_2$-CO$_2$H, at least one of B$^{2a}$ and B$^{2b}$ represents CF$_2$-PO$_3$H$_2$ or CF$_2$-CO$_2$H, and when one of B$^{2a}$ and B$^{2b}$ represents CF$_2$-CO$_2$H, at least one of B$^{1a}$ and B$^{1b}$ represents CF$_2$-PO$_3$H$_2$ or CF$_2$-CO$_2$H;

Hetcy is selected from the group consisting of:
(a) a 5–15 membered heteroaryl group containing 1–4 heteroatoms selected from O, S(O)y and N, wherein y is as defined above, and 0–2 carbonyl groups, optionally substituted with 1–4 members selected from R$^a$; and
(b) a non-aromatic carbocyclic structure containing 5–15 carbon atoms, interrupted by 1–4 heteroatoms selected from O, S(O)y wherein y is as previously defined, and N, and optionally containing 1–2 carbonyl groups, and optionally substituted with 1–4 members selected from R$^a$;

aryl is a 6–10 membered aromatic ring system that is optionally substituted with 1–4 members selected from R$^a$;

each R$^a$ is independently selected from the group consisting of: halo, NO$_2$, N$_3$, OH, CN, C(O)NH$_2$, C(O)NHC$_{1-3}$alkyl, C(O)N(C$_{1-3}$alkyl)$_2$, CO$_2$H, CO$_2$—C$_{1-10}$alkyl, C$_{1-10}$alkyl, C$_{1-10}$haloalkyl, C$_{1-10}$haloalkoxy, C$_{1-10}$alkoxy, C$_{1-10}$alkylthio, C$_{1-10}$alkylsulfinyl, C$_{1-10}$alkylsulfonyl, phenylsulfonyl and phenyl;

X is OH or NH$_2$,

Y is selected from the group consisting of: H, C$_{1-6}$alkyl, R$^1$ZCO—, R$^2$— and R$^3$S(O)$_2$—;

Z represents a bond or is selected from O, S(O)yCH$_2$, NR$^4$ or CH=CH;

R$^4$ represents H, C$_{1-6}$alkyl, Hetcy or aryl, said alkyl, Hetcy and aryl being optionally substituted with 1–3 members selected from R$^a$;

R$^1$ is selected from the group consisting of:
(a) C$_{1-10}$alkyl;
(b) C$_{1-6}$fluoroalkyl, optionally substituted with a hydroxy group;

(c) aryl optionally substituted with 1–3 substituents selected from $R^a$;

(d) heteroaryl, said heteroaryl group being a monocyclic aromatic ring of 5 atoms, said ring having one heteroatom which is O, S or N, and optionally 1, 2, or 3 additional N atoms; or a monocyclic ring of 6 atoms, said ring having one heteroatom which is O, S or N, and optionally 1, 2, or 3 additional N atoms, said heteroaryl group being optionally substituted with from 1–3 substituents selected from $R^a$;

(e) benzoheterocycle in which the heterocycle is a 5, 6, or 7-membered ring containing 1 or 2 heteroatoms selected from O, S and N, optionally containing a carbonyl, sulfinyl or sulfonyl group; said benzoheterocycle being optionally substituted with 1–3 substituents selected from $R^a$;

(f) a heterocycloalkyl group of 5, 6 or 7 members which contains 1 or 2 heteroatoms selected from O, S and N, and optionally containing a carbonyl group or a sulfonyl group;

(g) a benzocarbocycle in which the carbocycle is a 5, 6, or 7-membered ring which optionally contains a carbonyl group, optionally substituted with 1–2 substituents selected from $R^a$;

(h) a bicyclic heteroaryl group having 8, 9 or 10 members, containing 1 to 5 heteroatoms selected from O, S and N, optionally substituted with 1–2 substituents selected from Ra; and (i) hydrogen;

$R^2$ is the acyl residue of an amino acid, the amino group of which may be optionally substituted by an acyl group of the structure $R^1ZCO$— or $C_{1-6}$ alkyl, and in the case of a dicarboxylic amino acid, the terminal carboxyl may optionally be in the form of a $C_{1-4}$ alkyl ester;

$R^3$ is selected from the group consisting of:
  (a) $C_{1-10}$alkyl,
  (b) $C_{1-6}$fluoroalkyl, and
  (c) $C_{6-10}$aryl optionally substituted as defined above, and $R^5$ and $R^6$ independently represent members selected from the group consisting of: H, $C_{1-10}$alkyl, $C_{2-10}$alkenyl, aryl ,Hetcy, $CONH_2$, $CO_2H$, $CO_2$—$R^4$, $C(O)R^4$, $C_{1-6}$fluoroalkyl, said alkyl,aryl, and Hetcy groups being optionally substituted with 1–3 substituents selected from $R^a$;

or $R^5$ and $R^6$ are taken in combination and represent a 7 membered carbocyclic ring, optionally interrupted with 1–3 heteroatoms selected from O, S(O)y and N, and optionally substituted with 1–3 members selected from $R^a$.

The terms used herein have the following meanings unless otherwise specified.

Alkyl means $C_{1-10}$ linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0] decyl and the like.

Fluoroalkyl means alkyl groups of the indicated number of carbon atoms in which one or more hydrogens is replaced by fluorine. Examples are —$CF_3$, —$CH_2CH_2F$, —$CH_2CF_3$, c-Pr—$F_5$, c-Hex—$F_{11}$ and the like.

Aryl refers to $C_{6-14}$ aromatic lings and ring systems, having alternating or resonating double bonds. Examples include phenyl, biphenyl, naphthyl, anthracenyl and phenanthrenyl.

Heterocycle (Hetcy) as used herein refers to heterocyclic non-aromatic, partially aromatic and aromatic moieties, as well as aryl groups that are substituted with one or more heteroatom containing groups. One or two carbonyl groups may also be present. Thus, for example, heterocycle represents (a) a 5–15 membered heteroaryl group as defined below, containing 1–4 heteroatoms selected from O, S(O)y and N, wherein y represents 0, 1 or 2, and 0–2 carbonyl groups, optionally substituted with 1–4 members selected from the group consisting of: halo, $NO_2$, $N_3$, OH, CN, $C(O)NH_2$, $C(O)NHC_{1-3}$alkyl, $C(O)N(C_{1-3}$alkyl$)_2$, $CO_2H$, $CO_2$—$C_{1-10}$ alkyl, $C_{1-10}$ alkyl, $C_{1-6}$ fluoroalkyl, $C_{1-10}$ alkoxy, $C_{1-10}$ alkylthio, $C_{1-10}$ alkylsulfinyl, $C_{1-10}$ alkylsulfonyl and phenyl. Heterocycle also includes (b) a 6–10 membered aryl group that is substituted with 1–3 members selected from the group consisting of: $NO_2$, $NH_2$, $NHC_{1-3}$ alkyl, $N(C_{1-3}$alkyl$)_2$, $N_3$, OH, and $OC_{1-3}$ alkyl. Further, heterocycle includes non-aromatic heterocycles containing 5–15 atoms, 1–4 heteroatoms selected from O, S(O) y and N, and 0–2 carbonyl groups, optionally substituted with 1–4 members selected from the group consisting of: halo, $NO_2$, $N_3$, OH, CN, $C(O)NH_2$, $C(O)NHC_{1-3}$alkyl, $C(O)N(C_{1-3}$alkyl$)_2$, $CO_2H$, $CO_2$—$C_{1-10}$ alkyl, $C_{1-10}$ alkyl, $C_{1-6}$ fluoroalkyl, $C_{1-10}$ alkoxy, $C_{1-10}$ alkylthio, $C_{1-10}$ alkylsulfinyl, $C_{1-10}$ alkylsulfonyl and phenyl.

Examples of heterocycles include the following:

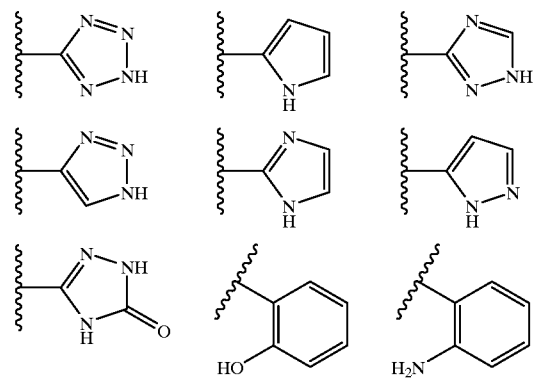

Heteroaryl, is a subset of heterocycle and refers to 5–15 membered aromatic ling systems having from 1–4 heteroatoms selected from O, S and N. Examples include furanyl, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, and triazolyl.

Benzoheterocycle is another subset of heterocycle, as in $R^1$ and $R^2$, includes, 2H-1-benzopyran-2-one, 4H-1-benzopyran-4-one, 2(3H)benzofuranone, 3(2H) benzofuranone, 2,3-dihydrobenzofuran, 2,3-dihydrobenzothiophene, indoline and related structures.

Heterocycloalkyl is another subset of heterocycle and includes non-aromatic heterocyclic moieties having from 4–15 atoms, with from 1–4 heteroatoms contained therein, selected from O, S and N. Examples include azetidine, pyrrolidine, piperidine, hexahydroazepine, tetrahydrofuran, tetiahydropyran, morpholine. thiomorpholine, piperazine, 2-oxopiperidine, 4-oxopiperidine, 2-oxotetrahydropyran and 4-oxotetrahydropyran.

Benzocarbocycle, refers to indane, 1,2,3,4-tetrahydronaphthalene and benzocycloheptene.

Bicyclic heteroaryl is another subset of heterocycle and refers to indole, benzofuran, benzothiophene, benzimidazole, benzoxazole, benzothiazole, benzotriazole, benzothiadiazole, quinoline, isoquinoline, pyrrolopyridine, furopyridine, and thienopyridine.

The following abbreviations have the indicated meanings:

| | |
|---|---|
| AA= | arachidonic acid |
| Ac= | acetyl |
| AIBN= | 2.2′-azobisisobutyronitrile |
| Bn= | benzyl |
| BSA= | bovine serum albumin |
| Bz= | benzoyl |
| CHO= | chinese hamster ovary |
| CMC= | 1-cyclohexyl-3-(2-morpholinoethyl) carbodiimidemetho-p-toluenesulfonate |
| DBU= | diazabicyclo[5.4.0]undec-7-ene |
| DMAP= | 4-(dimethylamino)pyridine |
| DMF= | N,N-dimethylformamide |
| DMSO= | dimethyl sulfoxide |
| Et$_3$N= | triethylamine |
| HBSS= | Hanks balanced salt solution |
| HEPES= | N$^1$-[2-Hydroxyethyl]piperazine-N$^4$-[2-ethanesulfonic acid] |
| HWB= | human whole blood |
| KHMDS= | potassium hexamethyldisilazane |
| LDA= | lithium diisopropylamide |
| LPS= | lipopolysaccharide |
| MCPBA= | metachloro perbenzoic acid |
| MMPP= | magnesium monoperoxyphthalate |
| Ms= | methanesulfonyl = mesyl |
| MsO= | methanesulfonate = mesylate |
| NBS= | N-bromosuccinimide |
| NCS= | N-chlorosuccinimide |
| NIS= | N-iodosuccinimide |
| NSAID= | non-steroidal anti-inflammatory drug |
| Oxone®= | potassium peroxymonosulfate |
| PCC= | pyridinium chlorochromate |
| PDC= | pyridinium dichromate |
| PTP= | protein tyrosine phosphatase |
| r.t.= | room temperature |
| rac.= | racemic |
| Tf= | trifluoromethanesulfonyl = triflyl |
| TFAA= | trifluoroacetic anhydride |
| TfO= | trifluoromethanesulfonate = triflate |
| THF= | tetrahydrofuran |
| TLC= | thin layer chromatography |
| Ts= | p-toluenesulfonyl = tosyl |
| TsO= | p-toluenesulfonate = tosylate |
| Tz= | 1H (or 2H)-tetrazol-5-yl |
| Alkyl group abbreviations | |
| Me= | methyl |
| Et= | ethyl |
| n-Pr= | normal propyl |
| i-Pr= | isopropyl |
| n-Bu= | normal butyl |
| i-Bu= | isobutyl |
| s-Bu= | secondary butyl |
| t-Bu= | tertiary butyl |
| c-Pr= | cyclopropyl |
| c-Bu= | cyclobutyl |
| c-Pen= | cyclopentyl |
| c-Hex= | cyclohexyl |
| Dose Abbreviations | |
| bid= | bis in die = twice daily |
| qid= | quater in die = four times a day |
| tid= | ter in die = three times a day |

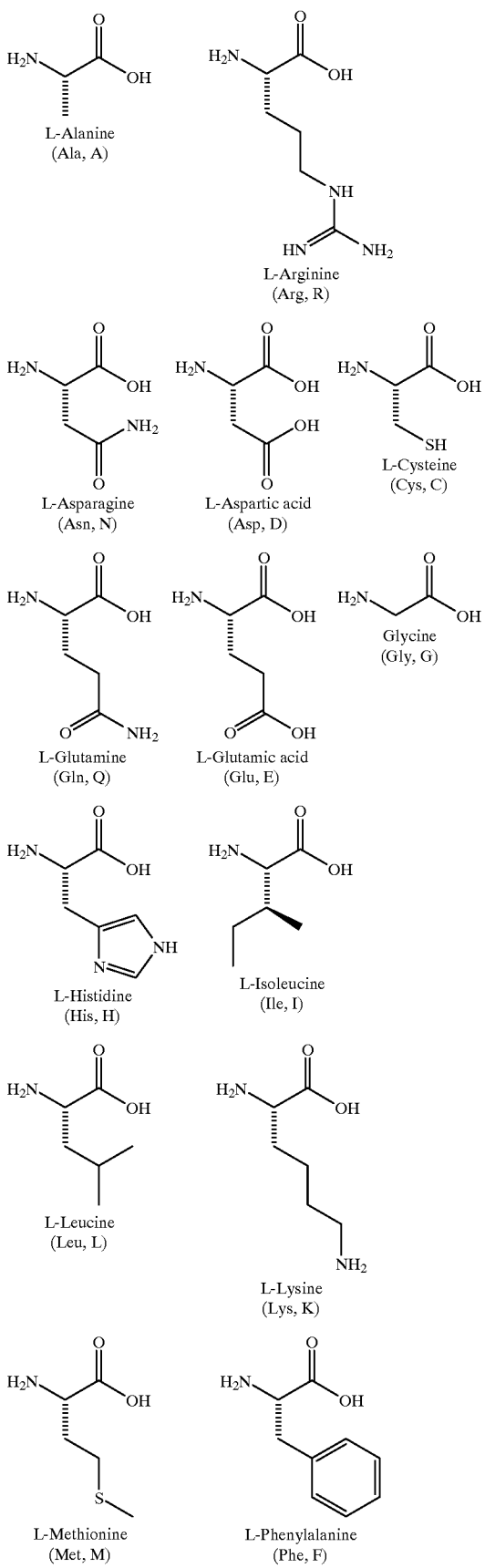

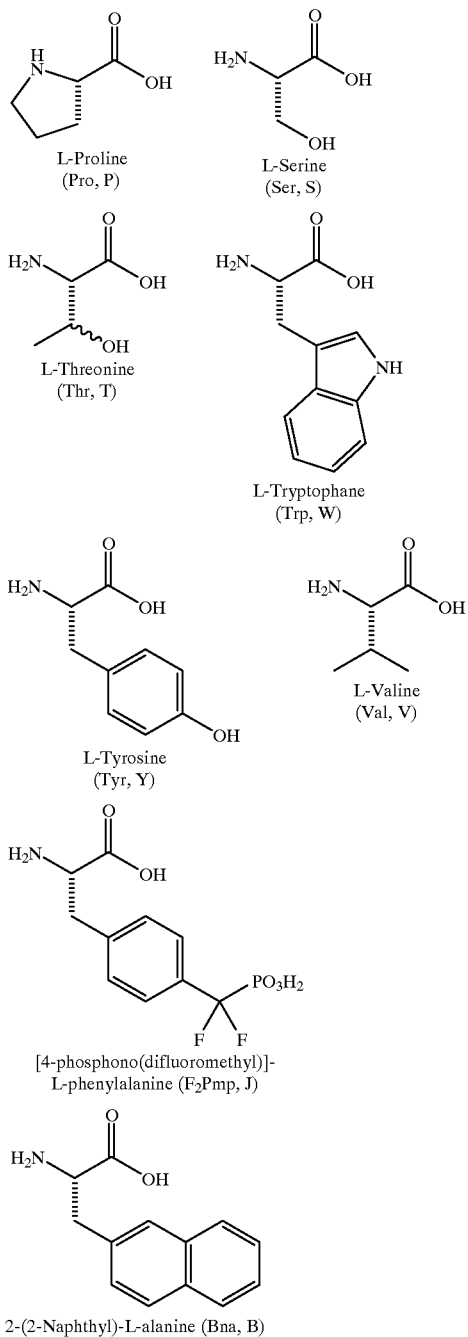

One aspect of the invention that is of particular interest relates to compounds of formula I wherein $B^{1a}$ represents $CF_2PO_3H_2$. Within this subset, all other variables are as originally defined.

Another subset of compounds that is of particular interest relates to compounds of formula I wherein $B^{2a}$ represents $CF_2CO_2H$. Within this subset, all other variables are as originally defined.

Another subset of compounds that is of particular interest relates to compounds of formula I wherein Y represents $R^1ZC(O)$— or $R^2$. Within this subset, all other variables are as originally defined.

More particularly, when Y represents $R^1ZC(O)$—, $R^1$ represents (c) a mono-, di- or tri-substituted aromatic hydrocarbon wherein the substituents are selected from the group consisting of
 (1) hydrogen,
 (2) halo,
 (3) $NO_2$,
 (4) $N_3$,
 (5) OH,
 (6) CN,
 (7) $CONH_2$,
 (8) $CO_2H$,
 (9) $CO_2$—$C_{1-10}$alkyl,
 (10) $C_{1-10}$ alkyl,
 (11) $C_{1-6}$ fluoroalkyl,
 (12) $C_{1-10}$alkoxy,
 (13) $C_{1-10}$alkylthio,
 (14) $C_{1-10}$alkylsulfinyl,
 (15) $C_{1-10}$alkylsulfonyl, or
 (16) phenyl;

(d) mono-, di- or tri-substituted heteroaryl wherein the heteroaryl is a monocyclic aromatic ring of 5 atoms, said ring having one heteroatom which is S, O or N, and optionally 1, 2, or 3 additional N atoms; or
the heteroaryl is a monocyclic ring of 6 atoms, said ring having one heteroatom which is N, and optionally 1, 2, or 3 additional N atoms, wherein the substituents are selected from the group consisting of
 (1) hydrogen,
 (2) halo,
 (3) $NO_2$,
 (4) $N_3$,
 (5) OH,
 (6) CN,
 (7) $CONH_2$,
 (8) $CO_2H$,
 (9) $CO_2$—$C_{1-10}$alkyl,
 (10) $C_{1-10}$ alkyl,
 (11) $C_{1-6}$ fluoroalkyl,
 (12) $C_{1-10}$alkoxy,
 (13) $C_{1-10}$alkylthio,
 (14) $C_{1-10}$ alkylsulfinyl, or
 (15) $C_{1-10}$alkylsulfonyl;

(e) a mono- or di-substituted benzoheterocycle in which the heterocycle is a 5, 6, or 7-membered ring which may contain 1 or 2 heteroatoms chosen independently from O, S, or N and which may contain a carbonyl group or a sulfonyl group; wherein the substituents are selected from the group consisting of:
 (1) hydrogen,
 (2) halo,
 (3) $NO_2$,
 (4) $N_3$,
 (5) OH,
 (6) CN,
 (7) $CONH_2$,
 (8) $CO_2H$,
 (9) $CO_2$—$C_{1-10}$alkyl,
 (10) $C_{1-10}$ alkyl,
 (11) $C_{1-6}$fluoroalkyl,
 (12) $C_{1-10}$alkoxy
 (13) $C_{1-10}$alkylthio,

(14) $C_{1-10}$alkylsulfinyl, and
(15) $C_{1-10}$alkylsulfonyl;

(f) a heterocycloalkyl group of 5, 6 or 7 members which contains 1 or 2 heteroatoms chosen from O, S, or N and optionally contains a carbonyl group or a sulfonyl group;

(g) a mono- or di-substituted benzocarbocycle in which the carbocycle is a 5, 6, or 7-membered ring which optionally contains a carbonyl group, wherein the substituents are selected from the group consisting of
(1) hydrogen,
(2) halo,
(3) $NO_2$,
(4) $N_3$,
(5) OH,
(6) CN,
(7) $CONH_2$,
(8) $CO_2H$,
(9) $CO_2$—$C_{1-10}$alkyl,
(10) $C_{1-10}$ alkyl,
(11) $C_{1-6}$ fluoroalkyl,
(12) $C_{1-10}$alkoxy,
(13) $C_{1-10}$alkylthio,
(14) $C_{1-10}$alkylsulfinyl, or
(15) $C_{1-10}$alkylsulfonyl;

or (h) a mono- or di-substituted bicyclic heteroaryl of 8, 9, or 10 members, containing 1 to 5 heteroatoms chosen independently from O, S or N, wherein the substituents are selected from the group consisting of
(1) hydrogen,
(2) halo,
(3) $NO_2$,
(4) $N_3$,
(5) OH,
(6) CN,
(7) $CONH_2$,
(8) $CO_2H$,
(9) $CO_2$—$C_{1-10}$alkyl,
(10) $C_{1-10}$alkyl,
(11) $C_{1-6}$ fluoroalkyl,
(12) $C_{1-10}$alkoxy,
(13) $C_{1-10}$alkylthio,
(14) $C_{1-10}$alkylsulfinyl, and
(15) $C_{1-10}$alkylsulfonyl. Within this subset, all other variables are as originally defined.

More particularly, when Y represents $R^1ZC(O)$—, Z represents $SCH_2$, $SO_2CH_2$ or a bond. Within this subset, all other variables are as originally defined.

More particularly, when Y represents $R^2$, $R^2$ represents the acyl residue of an amino acid, the amino group of which may be optionally substituted by an acyl group of the structure $R^1ZCO$— or $C_{1-6}$ alkyl, and in the case of a dicarboxylic amino acid. The terminal carboxyl may optionally be in the form of a $C_{1-4}$ alkyl ester.

Within this subset, all other variables are as originally defined.

Another preferred embodiment of the invention relates to compounds of formula Ia:

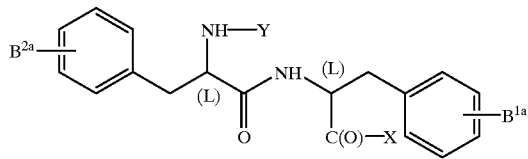

Within this subset, all variables are as originally defined.

Another preferred embodiment of the invention relates to compounds of formula I wherein $R^2$ represents an acyl residue of an amino acid in the L-configuration.

Another preferred embodiment of structure A is that wherein Z is a bond.

Another preferred embodiment of structure A is that wherein X is $NH_2$.

Exemplifying this invention are the following compounds:
(a) (4S)-5-[((1S)-2-[((1S)-2-amino-1-{4-[difluoro(phosphono)methyl]benzyl}-2-oxoethyl)amino]-1-{4-[carboxy(difluoro)methyl]benzyl}-2-oxoethyl)amino]-4-(benzoylamino)-5-oxopentanoic acid,
(b) (4S )-5-[((1S)-2-[((1S)-2-amino-1-{4-[carboxy(difluoro)methyl]benzyl}-2-oxoethyl)amino]-1-{4-[difluoro(phosphono)methyl]benzyl}-2-oxoethyl)amino]-4-(benzoylamino)-5-oxopentanoic acid:
(c) [4-((2S)-3-amino-2-{[(2S)-2-(benzoylamino)-3-(4-hydroxyphenyl)propanoyl]amino}-3-oxopropyl)phenyl](difluoro)methylphosphonic acid, and
(d) 2-{4-[(2S)-3-[((1S)-2-amino-1-{4-[difluoro(phosphono)methyl]benzyl}-2-oxoethyl)amino]-2-(benzoylamino)-3-oxopropyl]phenyl}-2,2-difluoroacetic acid.

The invention further encompasses a pharmaceutical composition which is comprised of a compound of formula I in combination with a pharmaceutically acceptable carrier.

More particularly, the pharmaceutical composition is comprised of a substantially non-toxic effective amount of a compound of claim 1 in combination with a pharmaceutically acceptable carrier.

Additionally, the invention described herein encompasses a method of treating a PTP-1B mediated disease comprising administering to a patient in need of such treatment a compound in accordance with formula I in an amount effective for treating said PTP-1B mediated disease.

Optical Isomers—Diastereomers—Geometric Isomers

The compounds described herein contain one or more asymmetric centers and thus give rise to diastereomers and optical isomers. The present invention includes all such possible diastereomers, as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The compounds and compositions of the present invention include pharmaceutically acceptable salts and hydrates. The composition may also contain other therapeutic ingredients.

When the compound of the present invention is basic salts may be prepared from pharmaceutically acceptable non-toxic acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetiaacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

In the discussion of methods of treatment which follows, references to the Compounds of formula I apply also include the pharmaceutically acceptable salts.

Utilities

The compounds of formula I inhibit PTP-1B and thus improve insulin-sensitivity. The compounds have utility in preventing or treating Type 1 and Type 2 diabetes, improving glucose tolerance, improving insulin-sensitivity when there is insulin-resistance and treating or preventing obesity. In addition, the compounds may be used to treat or prevent cancer, neurodegenerative diseases and the like.

Pharmaceutical Compositions

For the treatment of any of these PTP-1B-mediated diseases compound A may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, ot syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents. for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyccryl monostearate or glyceryl distearate may be employed. They may also be coated by the technique described in the U.S. Pat. Nos. 4,256,108; 4,166.452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipicnts suitable for the manufacture of aqueous suspensions. Such excipients are suspending agents, for example sodium carboxymethylcellulose, methylcellulose, hydroxy-propylmethycellulose, sodium alginate, polyvinyl-pyiolidone, gum tragacanth and gum acacia, dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloul-ing agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occuring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenter-ally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, cr-cams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dose Ranges

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula I are synthesized in accordance with the following synthetic schemes.

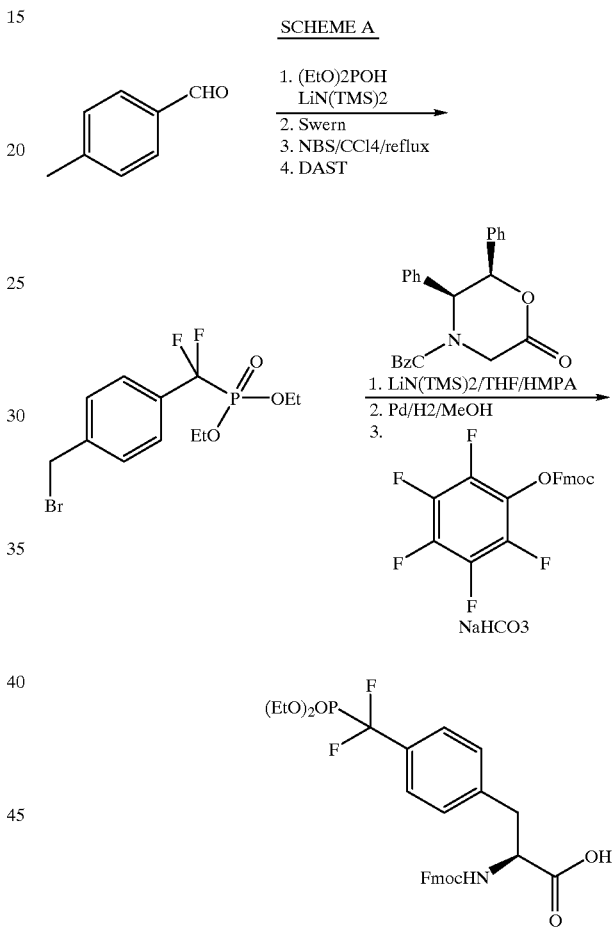

Method A

Diethyl phosphite can be deprotonated with a base such as LiN(TMS)$_2$ and reacted with tolualdehyde to provide an alcohol which may be oxidized with MnO$_2$ or Swern's conditions to give a phosphonoketone. Brominatiom of phosphonoketone with NBS followed by fluorination with DAST afford bromide which can be used to alkylated Benzyl(2R,3S)-(−)-6-oxo-2,3-diphenyl-4-moipholinc-caiboxylate. The resulting product is hydrogenalyzed with H$_2$ with palladium and protected with 9-Fluorenylmethyl pentafluorophenyl carbonate to yield Ib.

SCHEME B

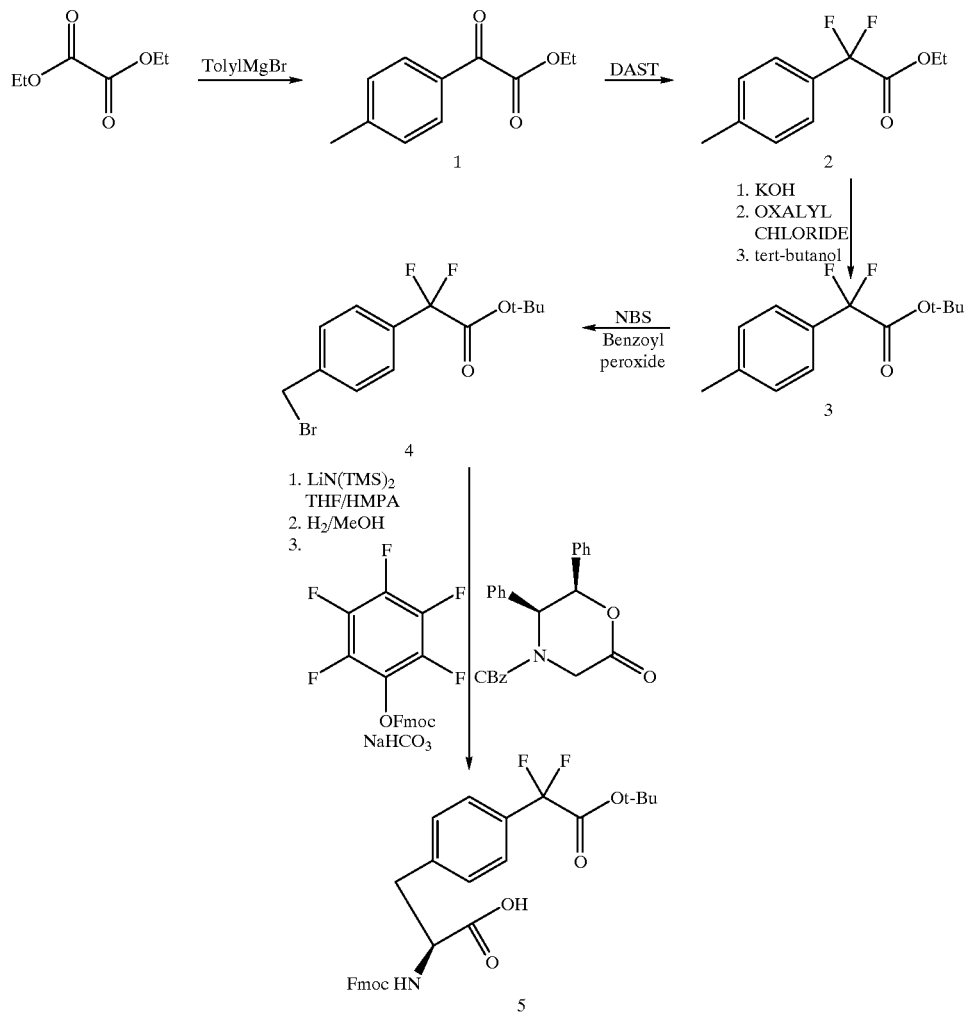

Method B

Diethyl oxalate can be reacted with tolylmagnesium bromide to provide tolylketoester 1 which is fluoronated with DAST leading to 2. Saponification followed by reaction with oxalyl chloride and tert-butanol give the tert-butyl ester 3. Bromination with NBS afford bromide 4 which can be used to alkylated Benzyl(2R,3S)-(−)-6-oxo-2,3-diphenyl-4-mopholine-cai-boxylate. The resulting product is hydrogenalyzed with $H_2$ with palladium and protected with 9-Fluorenylmethyl pentafluorophenyl carbonate to yield 5.

SCHEME C

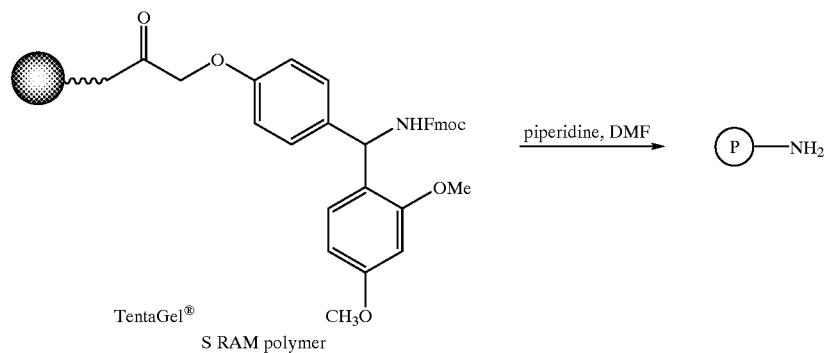

-continued
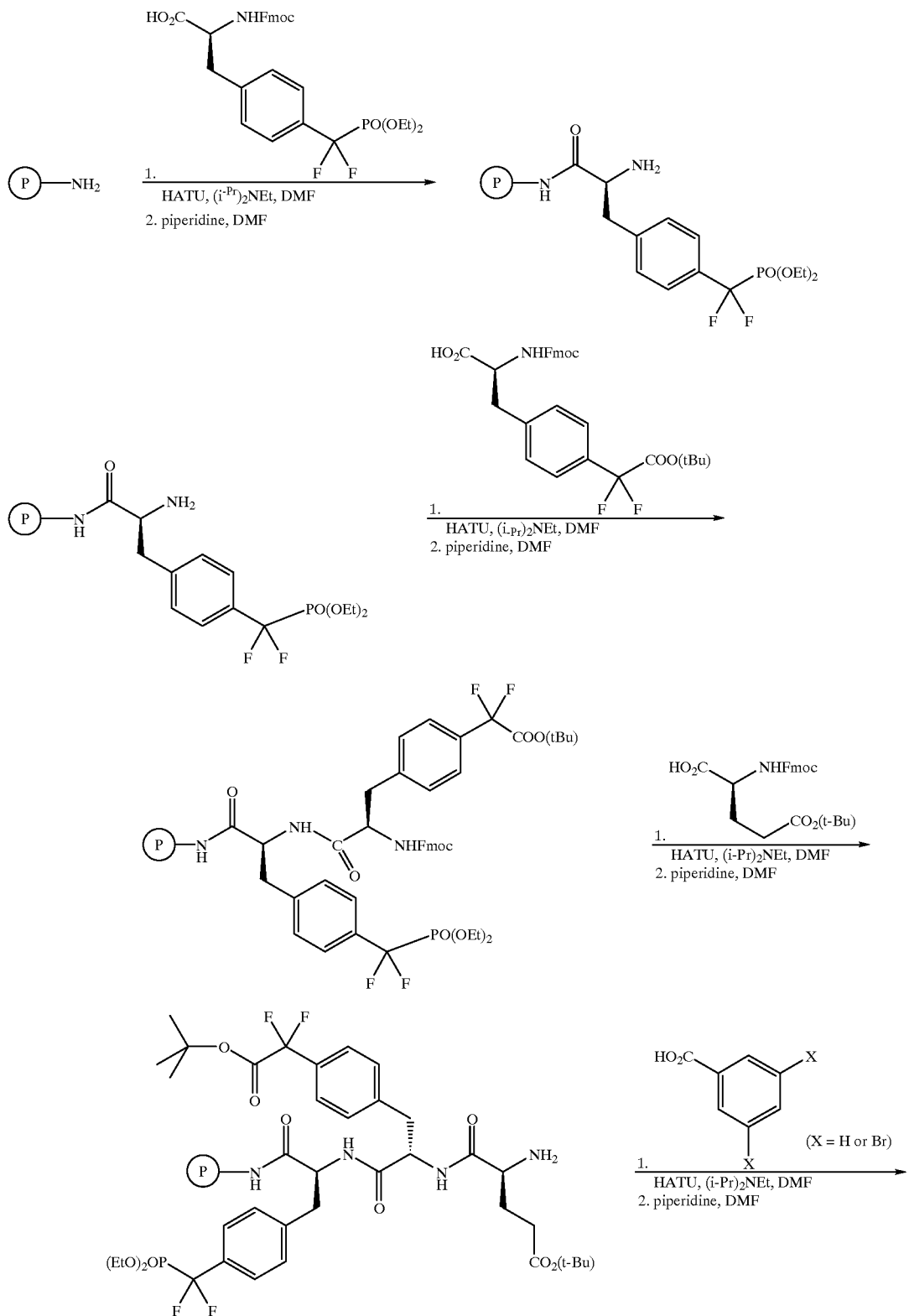

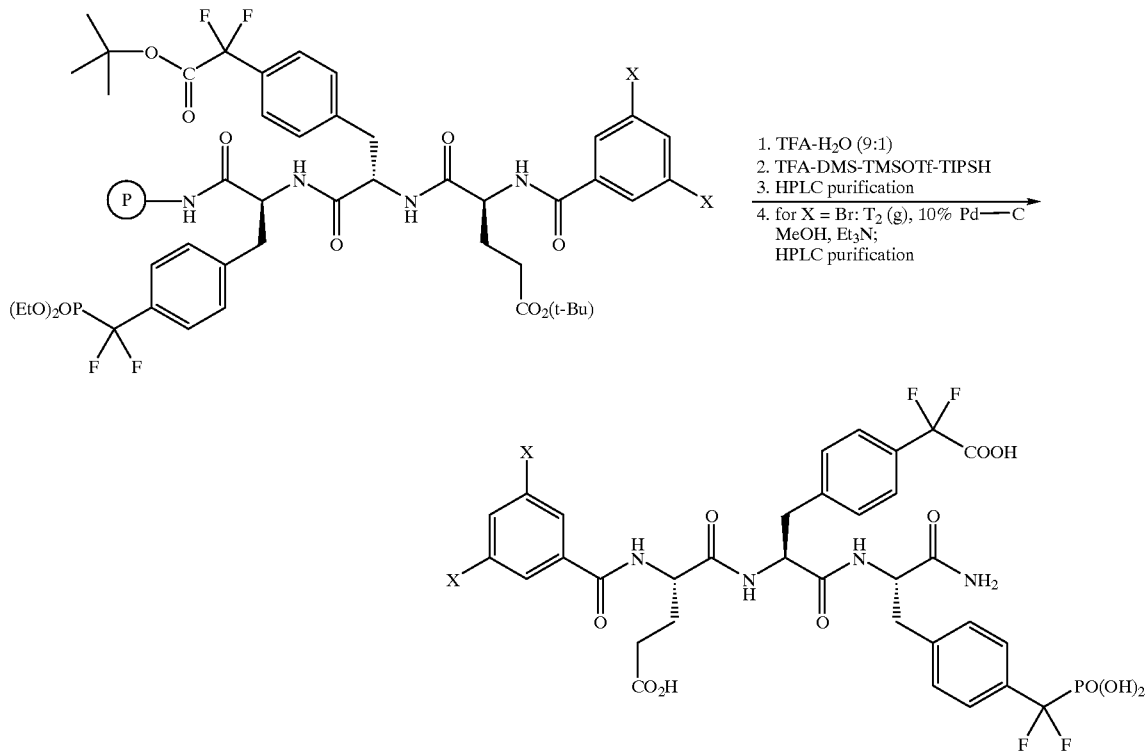
X = H or T
Representative Compounds
Table I illustrates compounds of formula I, which are representative of the present invention.
TABLE I
| | Example | Method |
|---|---|---|
| | 1 | A + B + C |

TABLE I-continued

| | Example | Method |
|---|---|---|
| (structure) | 2 | A + B + C |
| (structure) | 3 | A + B + C |
| (structure) | 4 | A + B + C |

TABLE I-continued
| | Example | Method |
|---|---|---|
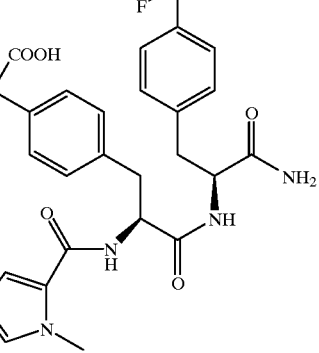
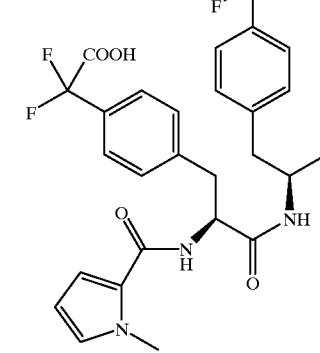
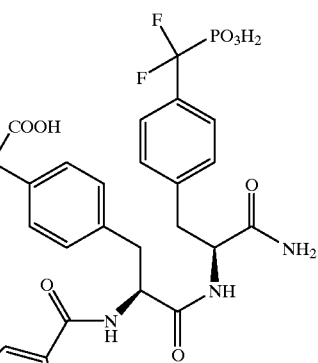
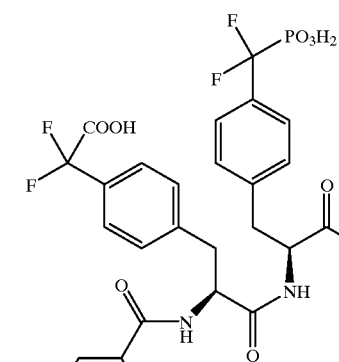
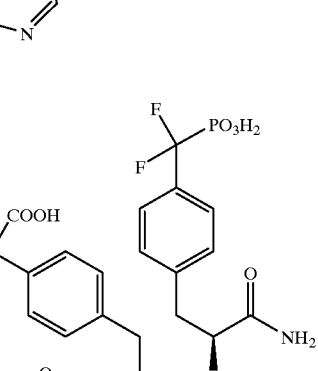
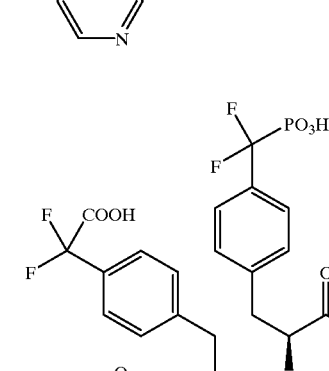

TABLE I-continued

| | Example | Method |
|---|---|---|

3

TABLE I-continued

| | Example | Method |
|---|---|---|

[Four chemical structures shown, each containing difluoromethylphosphonate-substituted phenylalanine and difluorocarboxylic acid-substituted phenylalanine dipeptide derivatives with varying N-terminal caps (phenylsulfonylacetyl or benzotriazole-carbonyl) and C-terminal groups (amide or carboxylic acid).]

Assays for Determining. Biological Activity

The compounds of Formula I can be tested using the following assays to demonstrate their PTP-1B-inhibiting activity.

Phosphatase Assay Protocol

Materials

EDTA-ethylenediaminetetraacetic acid (Sigma)

DMH-N,N'-dimethyl-N,N'-bis(mercaptoacetyl)-hydrazine (synthesis published in *J. Org. Chem.* 56, pp. 2332–2337, (1991) by R. Singh and G. M. Whitesides and can be substituted with DTT-dithiothreitol Bistris-2,2-bis(hydroxymethyl)2,2',2"-nitrilotriethanol- (Sigma) Triton X-100-octylphenolpoly(ethyleneclycolether) 10 (Pierce)

Antibody: Anti-glutathione S-transferase rabbit (H and L) fraction (Molecular Probes)

Enzyme: Human recombinant PTP1B, containing amino acids 1–320, (Seq. ID No. 1) fused to GST enzyme (glutathione S-transferase) purified by affinity chromatography. Wild type (Seq. ID No. 1) contains active site cysteine(215), whereas mutant (Seq. ID No. 7) contains active site serine(215).

Tritiated peptide: Bz-NEJJ-CONH$_2$, Mwt. 808, empirical formula, $C_{32}H_{32}T_2O_{12}P_2F_4$

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1X) (room temp.) 2 mM EDTA Enzyme Dilution | 50 mM Bistris 5 mM DMH (MW = 208) |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

IC$_{50}$ Binding Assay Protocol:

Compounds (ligands) which potentially inhibit the binding of a radioactive ligand to the specific phosphatase are screened in a 96-well plate format as follows:

To each well is added the following solutions @ 25° C. in the following chronological order:

1. 110 μl of assay buffer.
2. 10 μl. of 50 nM tritiated BzN-EJJ-CONH$_2$ in assay buffer (I×)@ 25° C.
3. 10 μl. of testing compound in DMSO at 10 different concentrations in serial dilution (final DMSO, about 5% v/v) in duplicate @ 25° C.
4. 10 μl. of 3.75 μg/ml purified human recombinant GST-PTP1B in enzyme dilution buffer.
5. The plate is shaken for 2 minutes.
6. 10 μl. of 0.3 μg/ml anti-glutathione S-transferase (anti-GST) rabbit IgG (Molecular Probes) diluted in antibody dilution buffer @ 25° C.
7. The plate is shaken for 2 minutes.
8. 50 μl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. IC$_{50}$ value is approximated from the non-linear regression fit with the 4-parameter/multiple sites equation (described in: "Robust Statistics", New York, Wiley, by P. J. Huber (198 1) and reported in nM units.
14. Test ligands (compounds) with larger than 90% inhibition at 10 μM are defined as actives.

| Enzyme Assay PTP1B | |
|---|---|
| Assay buffer | 50 mM Bis-Tris (pH = 6.3) |
| | 2 mM EDTA |
| | 5 mM N,N'-dimethyl-N,N'-bis(mercaptoacetyl)-hydrazine (DMH) |
| Substrate | 10 mM fluorescein diphosphate (FDP) store at −20° C. |
| Enzyme dilution buffer | 50 mM Bis-Tris (pH = 6.3) |
| | 2 mM EDTA |
| | 5 mM DMH |
| | 20% (v/v) glycerol |
| | 0.01% (v/v) BSA |

The assay is carried out at room temperature in 96 well plates. The reaction mixture in 180 μl contains 50 mM Bis-Tris (pH=6.3), 2 mM EDTA, 5 mM N,N'-dimethyl-N, N'bis(mercaptoacetyl)hydrazine (DMH) and 10 μM fluorescein diphosphare (FDP). 10 μl of 10 concentrations (serial dilution) of the test compound (inhibitor) dissolved in DMSO or DMSO alone for control is added to each well and the plate is mixed for 2 min. The reaction is initiated by adding 10 μl of diluted PTP1B (50 nM in 50 mM Bis/Tnis (pH=6.3), 2 mM EDTA, 5 mM DMH, 20% glycerol and 0.01% Triton X-100. The phosphatase activity is followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays are done at least in duplicate. The initial rate of FMP formation is plotted against the concentration of inhibitor and the data is fitted to a 4-parameter equation and the inflection point of the fit is the IC$_{50}$.

PHARMACOKINETICS IN RATS

Per Os Pharmacokinetics in Rats

PROCEDURE

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

PEG 200/300/400: restarted to 2 mL/kg

Methocel 0.5%–1.0%: 10 mL/kg

Tween 80: 10 mL/ka

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv\,(mg/kg)}{AUCiv}$$

The units of CL are mL/h·kg (milliliters per hour kilogram)

Intravenous Pharmacokinetics in Rats

PROCEDURE

The animals are housed, fed and cared for according to the Guidelines of the Canadian Council on Animal Care.

Male Sprague Daiwley (325–375 g,) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting, reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles:

The following vehicles may be used in IV rat blood level determinations:

| | |
|---|---|
| Dextrose: | 1 mL/kg |
| 2-Hydroxypropyl-β-cyclodextrin | 1 mL/kg |
| DMSO (dimethylsulfoxide): | Restricted to a dose volume of 0.1 mL per animal |
| PEG 200: | Not more than 60% mixed with 40% sterile water - 1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv\,(mg/kg)}{AUCiv}$$

The units of CL are mL/h·kg (milliliters per hour kilogram)

EXAMPLES

The invention is further illustrated by the following non-limiting examples in which, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C.

(iii) the course of reactions was followed by thin layer chromatography (TLC) and reaction times are given for illustration only;

(iv) melting points are uncollected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (litre(s)), mL (millilitres), g (gram(s)), mg (milligrams(s)), mol (moles), mmol (millimoles), eq (equivalent(s)).

Example 1

(4S)-5-[((1S)-2-[((1S)-2-AMINO-1-{4-[DIFLUORO (PHOSPHONO)METHYL]BENZYL}-2-OXOETHYL)AMINO]-1-{4-[CARBOXY (DIFLUORO)METHYL]BENZYL}-2-OXOETHYL)AMINO]-4-(BENZOYLAMINO)-5-OXOPENTANOIC ACID

Step 1 tert-Butyl 2-{4-(bromomethyl)phenyl}-2,2-difluoroacetate

To tert butyl 2-{4-(methyl)phenyl}-2,2-difluoroacetate (see X. Creary, *J. Org. Chem.* 1987, 52, 5026) (4.8 g) in CC14 (80 mL) was added NBS (3.8 g), followed by benzoyl peroxide (100 mg). The reaction mixture was heated at reflux and was irradiated with a sun lamp for 1.5 h. The mixture was cooled down and diluted with hexane (50 mL) purified by filtration on a pad of silica gel. The filtrate was concentrated to give the title product for step 2 as a yellow-brown liquid (6.4 g) $^1$H NMR δ: ($CD_3COCD_3$), 1.48 (9H, m), 4.70 (2H, s), 7.62 (4H, m).

Step 2 tert-Butyl 2-[4-({(3R, 5S, 6R)-4-{(benzyloxy) carbonyl}-2-Oxo-5,6-Diphenyl-1,4-Oxazinan-3-yl}methyl) Phenyl]-2,2-Difluoroacetate To a cooled solution at −78° C. of benzyl (2R, 3S)-(−)-6 oxo-2,3 diphenyl-4 morpholine carboxylate (10.5 g) and tert butyl 2-{4-(bromomethyl)phenyl}-2,2-difluoroacetate (6.2 g) and HMPA 55 mL in THF 550 ml. was added LiHMDS (28 mL, 1 M in THF) over a period of 1 hour 20 minutes. The reaction mixture was stirred further at −78° C. for 1 hour.

The reaction mixture was quenched with 200 mL of saturated $NH_4Cl$ diluted with 200 mL $H_2O$ and extracted with 500 mL hexane ethyl acetate 3:1. The mixture was dried over $MgSO_4$ and concentrated. The residue was flash chromatographed on silica using hexane and ethyl acetate 4:1 as eluant to give 4.1 g for step 3.

$^1$H NMR (CD$_3$COCD$_3$) δ: 1.45 (9H, s), 3.50–3.70 (2H, m), 4.95–5.22 (3H, m), 5.38 (1H, m), 5.55 (1H, d), 6.60 (2H, m), 6.82–7.00 (3H, m), 7.05–7.30 (9H, m), 7.35–7.45 (2H, m), 7.48–7.65 (3H, m).

Step 3 N -Fmoc-(2R)-2-amino-3{4[(tertbutyloxycaibonyl) (difluoro)methyl]phenyl}propanoic acid To tert butyl 2-[4({(3R, 5S, 6R)-4-{(benzyloxy) carbonyl}-2 Oxo-5,6-diphenyl-1,4-oxazinan-3-yl}methyl) Phenyl]-2,2-Difluoroacetate(3.7 g) in MeOH 40 mL and THF 20 mL was added Pd/C 10%, 0.8 g. The resulting mixture was hydrogenated using a Parr apparatus at 50 psi for 20 hours. The reaction mixture was then diluted with 200 mL MeOH and filtered through a pad of celite, and concentrated to give product (2.8 g)

$^1$H NMR ((CD$_3$)$_2$SO) δ: 1.42 (9H, s), 2.90–2.98 (1H, m), 3.10–3.22 (1H, m), 7.42 (4 H, m).

To (1 g suspended in dioxane) H$_2$O 40 mL was added NaHCO$_3$ (0.8 g) and 9-fluorenyl methyl pentafluorophenyl carbonate 0.82 g. The reaction mixture was stirred for 12 h at room temperature. The reaction was quenched by adding a NaCl solution 50 mL with acetic acid 2 mL and was extracted with hexane ethyl acetate 1:1. Dried over MgSO$_4$ and concentrated. The residue was flash chromatographed using a silica gel hexane, ethyl acetate 3:2 as eluant to give the titled compound 1.2 g as an oil for step 4.

$^1$H NMR (CD$_3$COCD$_3$) δ: 1.45 (9H, s), 3.12 (1H, m), 3.30 (1H, m), 4.18 (1H, m), 4.28 (2H, m), 4.52 (1H, m), 6.78 (1H, d), 7.30 (2H, m), 7.40 (2H, m), 7.50 (4H, m), 7.62 (2H, m), 7.85 (2H, d).

Step 4

5.0 g of Tentagel® RAM resin (RAPP polymer; 0.2 mmol/g) as represented by the shade bead in Scheme 1, was treated with piperidine (5 mL) in 20 mL of DMF for 30 min. The resin (symbolized by the circular P, containing the remainder of the organic molecule except the amino group) was dried with N$_2$ and washed successively with DMF (5×20 mL) and CH$_2$Cl$_2$ (5×20 mL). To a DMF (15.0 mL) solution of N α Fmoc-4-(diethyl) phosphono-(difluomethyl)]-L-phenylalanine (see D. Solas, *J. Org. Chem.*, 1996, 61, 1537) 0.900 g and 0-(7-azabenzotrazol-1-yl)-1, 1, 3, 3-tetrane-thyl uronium hexafluorphosphate (HATU) 0.600 g was added diisopropylethylamine (0.545 mL). After a period of 15 min, the mixture was added to the resin in DMF (15.0 mL). After a period of 45 min. the resin was washed with DMF (5×20 mL) and CH$_2$Cl$_2$ (5×20 mL). The resin was then treated with acetylimidazole (1.5 g) in DMF (15 mL). After a period of 1 h, the resin was washed successively in the DMF (5×20 mL) and CH$_2$Cl$_2$ (5×20 mL) and dried with nitrogen for the next step 5.

Step 5

After removal of the FMOC as described above, the second amino-acid is coupled to N Fmoc-(2R)2amino3{4 [(tertbutyloxycarbonyl) (difluoro)methylphenyl}propanoic acid 0.140 g and HATU 0.100 g in 5 mL DMF was added diisopropylphenyl amine (90 μL). After a period of 15 min., the mixture was added to the resin of step 1 0.86 g in DMF (10 mL). After a period of 45 min. the resin was washed with DMF (5×20mL) and CH$_2$Cl$_2$ (5×20 mL). The resin was then treated with piperidine (5 mL in DMF (20 mL) for a period of 0.5 h and was then washed successively with DMF (5×20 mL) and CH$_2$Cl$_2$ (5×20 mL) and dried with nitrogen for step 6.

Step 6

To a DMF solution (15 mL) of N-Fmoc-L-glutamic acid-t-butyl ester (0.374 g) and HATU (0.343 g) was added diisopylethylamine (0.311 mL). After a period of 15 min, the mixture was added to the resin of step 2 0.86 g in DMF (15 mL). After a period of 45 min. the resin was washed with DMF (5×20 mL) and CH$_2$Cl$_2$ (5×20 mL). The resin was then treated with pipetidine (5 mL) in DMF (20 mL) for a period of 0.5 h and was then washed successively with DMF (5×20 mL) and CH$_2$Cl$_2$ (5×20 mL) and dried with nitrogen for step 7.

Step 7

To a solution of benzoic acid (0.100 g) and HATU. (0.310 g) in DMF (10 mL) was added diisopropylethyl amine (0.284 mL). After a period of 15 min. the mixture was added to the resin of step 3 0.86 g in DMF (5 mL). After a period of 90 min. the resin was washed successively with DMF (5×10 mL) and CH$_2$Cl$_2$ (5×10 mL) and dried with nitrogen. The resin was treated with 10 mL of a mixture of TFA: water (9: 1) and 0.05 mL of triisopropylsilane for 30 min. The resin was filtered off and the filtrate was evaporated and co-distilled with water. The residue was treated with 2.5 mL of a mixture of TFA:DMS:TMSOTf (5:3:1) and 0.05 mL of triisopropylsilane and stirred at 25° C. for 15 h. The title compound was purified by reverse phase HPLC (C18 column. 40×100 mm) using a mobile phase gradient from 0.5% TFA in water to 50/50 acetonitrile/0.5% TFA in water over 30 min and monitoring at 235 nm.

$^1$H NMR (CD$_3$OD) C) δ 1.95–2.10 (2H, m), 2.38 (2H, t), 2.90–3.05 (2H, m), 3.05 (2H, m), 4.48 (1H, dd), 4.6 (1H, m), 7.28 (4H, dd), 7.40–7.55 (7H, m), 7.85 (2H, d).

Example 2

(4S)-5-[((1S)-2-[((1S)-2-Amino-1-{4-]caboxy (difluoro)methyl]benzyl}-2-oxoethyl)amino]-1-{4-[difluoro(phosphono)methyl]benzyl}-2-oxoethyl) amino]-4-(benzoylamino)-5-oxopentanoic Acid Step 1

2.0 g of Tentagel® S RAM resin (RAPP polymer, 0.2 mmole (g) as represented by shade bead in Scheme was treated with piperdine (5 mL) in 20 mL in 20 mL of DMF for 30 min. The resin (symbolized by the circular P), containing the remainder of the organic molecule except the amino group) was dried with N$_2$ and washed successively with DMF (5×20 mL) and CH$_2$Cl$_2$ (5×20 mL). To a DMF (15.0 mL) solution of N Fmoc-(2R)-2 amino-3{4 [(tertbutyloxycarbonyl)(difluoro) methyl]phenyl}propanoic acid (0.650 g) and HATU (0.800 g) was added diisopropylethylanine (0.650 mL). After a period of 15 min. the mixture was added to the resin in DMF (150 mL). After a period of 45 min. the resin was washed with DMF (5×20 ml,) and CH$_2$Cl$_2$ (5×20 mL). The resin was then dried with nitrogen. After removal of the Fmoc as described above, the second amino-acid is coupled in step 2.

Step 2

To a DMF (150 mL) solution of N α-Fmoc-4-[diethyl phosphono(difluoromethyl)]-L-phenylalanine (see D soles, *J. Org. Chem.*, 1996, 61, 1537) (0.20 g) and HATU (0.20 g) was added diisopropylethylanine (0.183 mL). After a period of 15 min. the mixture was added to the resin of step 1, 1.00 g in DMF (10 mL). After a period of 45 min. the resin was washed with DMF (5×20 mL) and CH$_2$Cl$_2$ (5×20 mL). The resin was then treated with piperidine (5 mL) in DMF (20 mL) for a period of 0.5 h and was then washed successively with DMF (5×20 mL) and CH$_2$Cl$_2$ (5×20 mL) and dried with nitrogen for step 3.

Step 3

To a DMF solution (15 mL) of N-Fmoc-L-glutamic acid-t-butyl ester (0.65 g) and HATU (0.95 g) was added diisopropylethylamine (0.85 mL). After a period of 15 min.

the mixture was added to the resin of step 2 (1 g) in DMF (15 mL). After a period of 45 min. the resin was washed with DMF (5×20 mL) and CH$_2$Cl$_2$ (5×20 mL). The resin was then treated with pipenidine (5 mL) in DMF (20 mL) for a period of 0.5 h and was then washed successively with DMF (5×20 mL) and CH$_2$Cl$_2$ (5×20 mL) and dried with nitrogen for step 4.

Step 4

To a solution of benzoic acid (0.244 g) and HATU (1.14 g) in DMF (10 mL) was added diusopropylethylanine (1.04 mL). After a period of 15 min. the mixture was added to the resin of step 3 (1 g) in DMF (5 mL). After a period of 90 min. the resin was washed successively with DMF (5×10 mL) and CH$_2$Cl$_2$ (5×10 mL) and dried with nitrogen. The resin was treated with acetylimidazole (1.5 g) in DMF (15 mL) in DMF (15 mL). After a period of 1 h, the resin was washed successively in the DMF (5×20 mL) and CH$_2$Cl$_2$ (5×20 mL) and dried with nitrogen. The resin was treated with 10 mL of a mixture of TFA: water (9:1) and 0.05 mL of triisopropylsilane for 30 min. The resin was filtered off and the filtrate was evaporated and co-distilled with water. The residue was treated with 2.5 mL of a mixture of TFA:DMS:TMSOTf (5:3:1) and 0.05 mL of triisopr-opylsilane and stirred at 25° C. for 15 h. The title compound was purified by reverse phase HPLC (C18 column, 40×100 mm) using a mobile phase gradient from 0.5% TFA in water to 50/50 acetonitrile/0.5% TFA in water over 30 min and monitoring at 235 nm.

$^1$H NMR (CD$_3$OD) δ: 1.95–2.10 (2H, m), 2.38 (2H, t), 2.90–3.05 (2H, m), 3.05 (2H, m), 4.48 (1H, dd), 4.6 (1H, m), 7.28 (4H, dd), 7.40–7.55 (7H, m), 7.85 (2H, d).

Example 3

[4-((2S)-3-Amino-2-{[(2S)-2-(benzoylamino)-3-(4-hydroxyphenyl)propanoyl]amino}-3-oxopropyl) phenyl](difluoro)methylphosphonic Acid Step 1

5.0 g of Tentagel® RAM resin (RAPP polymer; 0.2 mmol/g) as represented by the shade bead in Scheme 1, was treated with piperidine (5 mL) in 20 mL of DMF for 30 min. The resin (symbolized by the circular P. containing the remainder of the organic molecule except the amino group) was dried with N$_2$ and washed successively with DMF (5×20 mL) and CH$_2$Cl$_2$ (5×20 mL). To a DMF (15.0 mL) solution of N α Fmoc-4-(diethyl)phosphono-(difluomethyl)]-L-phenylalanine (see D. Solas, J. Org. Chem., 1996, 61, 1537) 0.900 g and 0-(7-azabenzotriazol-1-yl)-1, 1, 3, 3-tetrane-thyl uronium hexafluorphosphate (HATU) 0.600 g was added diusopropylethylamine (0.545 mL). After a period of 15 min. the mixture was added to the resin in DMF (15.0 mL). After a period of 45 min. the resin was washed with DMF (5×20 mL) and CH$_2$Cl$_2$ (5×20 mL). The resin was then treated with acetylimidazole (1.5 g) in DMF (15 ml,). After a period of 1 h, the resin was washed successively in the DMF (5×20 mL) and CH$_2$Cl$_2$ (5×20 mL) and dried with nitrogen for step 2.

Step 2

To a DMF (15 mL) solution of N-α-Fmoc-Tyr (tBu)-OH (1.20 g) and HATU (1.00 g) was added diisopropylethyl amine (0.91 mL). After a period of 15 min. the mixture was added to the resin of step 1 in DMF (15 mL). After a period of 45 min. the resin was washed with DMF (5×20 mL) and CH$_2$Cl$_2$ (5×20 mL). The resin was then treated with piperidine (5 mL) in DMF (20 mL) for a period of 0.5 h, and was then washed successively with DMF (5×20 mL) and CH$_2$Cl$_2$ (5×20 mL) and dried with nitrogen for step 3.

Step 3

To a solution of benzoic acid (0.244 g) and HATU (1.14 g) in DMF (10 mL) was added dilsopropylethylanine (1.04 mL). After a period of 15 min. the mixture was added to the resin of step 3 (1 g) in DMF (5 mL). After a period of 90 min. the resin was washed successively with DMF (5×10 mL) and CH$_2$Cl$_2$ (5×10 mL) and dried with nitrogen. The resin was treated with acetylimidazole (1.5 g) in DMF (15 mL) in DMF (15 mL). After a period of 1 h, the resin was washed successively in the DMF (5×20 mL) and CH$_2$Cl$_2$ (5×20 mL) and dried with nitrogen. The resin was treated with 10 mL of a mixture of TFA: water (9:1) and 0.05 mL of triisopropylsilane for 30 min. The resin was filtered off and the filtrate was evaporated and co-distilled with water and stirred at 25° C. for 15 h. The title compound was purified by reverse phase HPLC (C18 column, 40×100 mm) using a mobile phase gradient from 0.5% TFA in water to 50/50 acetonitrile/0.5% TFA in water over 30 min and monitoring at 235 nm.

$^1$H NMR (CD$_3$OD) δ: 2.85–3.20 (2H, m), 4.60 (1H, dd), 4.70 (1H, dd), 6.62 (2H, d), 7.05 (2H, d), 7.30 (2H, d), 7.45–7.55 (5H, m), 7.68 (2H, d).

Example 4

2-{4-[(2S)-3-[((1S)-2-Amino-1-{4-[difluoro (phosphono)methyl]benzyl}-2-oxoethyl)amino]-2-(benzoylamino]-3-oxopiopyl]phenyl}-2,2-difluoroacetic Acid Step 1

5.0 g of Tentagel® RAM resin (RAPP polymer; 0.2 mmol/g) as represented by the shade bead in Scheme 1, was treated with piperidine (5 mL) in 20 mL of DMF for 30 min. The resin (symbolized by the circular P, containing the remainder of the organic molecule except the amino group) was dnied with N$_2$ and washed successively with DMF (5×20 mL) and CH$_2$Cl$_2$ (5×20 mL). To a DMF (15.0 mL) solution of N α Fmoc-4-(diethyl)phosphono-(difluomethyl)]-L-phenylalanine (see D. Solas, J. Org. Chem., 1996, 61, 1537) 0.900 g and 0-(7-azabenzotilazol-1-yl)-1, 1, 3, 3-tetrane-thyl uronium hexafluorphosphate (HATU) 0.600 g was added diisopropylethylamine (0.545 mL). After a perios of 15 min. the mixture was added to the resin in DMF (15.0 mL). After a period of 45 min. the resin was washed with DMF (5×20 mL) and CH$_2$Cl$_2$ (5×20 mL). The resin was then treated with acetylimidazole (1.5 g) in DMF (15 ml). After a period of 1 h, the resin was washed successively in the DMF (5×20 mL) and CH$_2$Cl$_2$ (5×20 mL) and dried with nitrogen for step 2.

Step 2

After removal of the FMOC as described above, the second amino-acid is coupled to N-Fmoc-(2R)-2 amino-3{4 [(tertbutyloxycarbonyl)(difluolo) methyl]phenyl}propanoic acid 0.140 g and HATU 0.100 g in 5 mL DMF was added diisopropylethyl amine (90 µL). After a period of 15 min., the mixture was added to the resin of step 1, 0.86 g in DMF (10 ml). After a period of 45 min. the resin was washed with DMF (5×20 mL) and CH$_2$Cl$_2$ (5×20 ml).

The resin was then treated with piperidine (5 mL, in DMF (20 mL) for a period of 0.5 h and was then washed successively with DMF (5×20 mL) and CH$_2$Cl$_2$ (5×20 mL) and dried with nitrogen for step 3.

Step 3

To a solution of benzoic acid (0.100 g) and HATU. (0.310 g) in DMF (10 mL) was added diisopropylethyl amine (0.284 mL). After a period of 15 min. the mixture was added to the resin of step 3 0.86 g in DMF (5 mL). After a period of 90 min. the resin was washed successively with DMF (5×10 mL) and CH$_2$Cl$_2$ (5×10 mL) and dried with nitrogen.

The resin of step 2 was treated with 10 ml of a mixture of TFA: water (9:1) and 0.05 mL of tniisopropylsilane for 30 min. The resin was filtered off and the filtrate was evaporated and co-distilled with water. The residue was treated with 2.5 mL of a mixture of TFA:DMS:TMSOTf (5:3:1) and 0.05 mL of triisopropylsilane and stirred at 25° C. for 15 h. The title compound was purified by reverse phase HPLC (C18 column, 40×100 mm) using a mobile phase gradient from 0.5% TFA in water to 50/50 acetonitrile/0.5% TFA in water over 30 min and monitoring at 235 nm to give 10 mg.
$^1$H NMR (CD$_3$OD) δ: 2.95–3.10 (2H,m), 3.20 (2H, m ), 4.62 (1H, m), 7.25–7.50 (11H,m ), 7.65 (2H,d).

What is claimed is:

1. A compound represented by formula I:

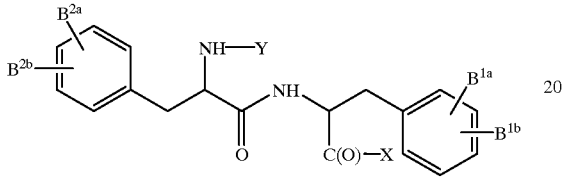

or a pharmaceutically acceptable salt or hydrate thereof wherein:
at least one of $B^{1a}$, $B^{1b}$, $B^{2a}$ and $B^{2b}$ represents $CF_2$—$PO_3H_2$ or $CF_2$—$CO_2H$,
at least one of $B^{1a}$, $B^{1b}$, $B^{2a}$ and $B^{2b}$ represents H, and the others are selected from the group consisting of:
$R^4$, OH, halo, $CHF_2$, $CF_3$, $CHF$—$CO_2H$, $CF_2$—$CO_2H$, $CF_2$—$C(R^5)(R^6)OH$, $CHF$—$PO_3H_2$, $CH_2$—$PO_3H_2$, $C(R^5)(R^6)OH$, $S(O)yR^5$, wherein y is 0, 1 or 2, $S(O)_2NR^5R^6$, $CFHSO_3H$, $CF_2SO_3H$, $CFHS(O)_2NR^5R^6$, $CF_2S(O)_2$ $NR^5R^6$, $NR^6S(O)_2R^5$, CFH-Hetcy, $CF_2$-Hetcy, $CH_2S(O)_2$-Hetcy, $CFHS(O)_2$-Hetcy, $CF_2S(O)_2$-Hetcy, $CH_2S$-Hetcy, CFHS-Hetcy, $CF_2S$-Hetcy, $OC(R^5)(R^6)F$, $C(R^5)(R^6)$ F, O—$CF_2CO_2R^4$, O—$CH_2CO_2R^4$, $C(R^5)(R^6)$ $CO_2R^4$, $CO_2R^4$, CFH-aryl, $CF_2$-aryl, $CH_2S(O)_2$-aryl, $CFHS(O)_2$-aryl, $CF_2S(O)_2$-aryl, $CH_2S$-aryl, CFHS-aryl and $CF_2S$-aryl;
such that when one of $B^{1a}$ and $B^{1b}$ represents $CF_2$—$CO_2H$, at least one of $B^{2a}$ and $B^{2b}$ represents $CF_2$—$PO_3H_2$ or $CF_2$—$CO_2H$, and when one of $B^{2a}$ and $B^{2b}$ represents $CF_2$—$CO_2H$, at least one of $B^{1a}$ and $B^{1b}$ represents $CF_2$—$PO_3H_2$ or $CF_2$—$CO_2H$;
Hetcy is selected from the group consisting of:
(a) a 5–15 membered heteroaryl group containing 1–4 heteroatoms selected from O, $S(O)_y$ and N, wherein y is as defined above, and 0–2 carbonyl groups, optionally substituted with 1–4 members selected from $R^a$; and
(b) a non-aromatic carbocyclic structure containing 5–15 carbon atoms, interrupted by 1–4 heteroatoms selected from O, $S(O)_y$ wherein y is as previously defined, and N, and optionally containing 1–2 carbonyl groups, and optionally substituted with 1–4 members selected from $R^a$;
aryl is a 6–10 membered aromatic ring system that is optionally substituted with 1–4 members selected from $R^a$;
each $R^a$ is independently selected from the group consisting of: halo, $NO_2$, $N_3$, OH, CN, $C(O)NH_2$, $C(O)NHC_{1-3}$alkyl, $C(O)N(C_{1-3}$alkyl$)_2$, $CO_2H$, $CO_2$—$C_{1-10}$alkyl, $C_{1-10}$alkyl, $C_{1-10}$ haloalkyl, $C_{1-10}$haloalkoxy, $C_{1-10}$alkoxy, $C_{1-10}$alkylthio, $C_{1-10}$ alkylsulfinyl, $C_{1-10}$alkylsulfonyl, phenylsulfonyl and phenyl;
X is OH or $NH_2$,
Y is selected from the group consisting of: H, $C_{1-6}$alkyl, $R^1$ZCO—, $R^2$— and $R^3S(O)_2$—;
Z represents a bond or is selected from O, $S(O)yCH_2$, $NR^4$ or CH=CH;
$R^4$ represents H, $C_{1-6}$alkyl, Hetcy or aryl, said alkyl, Hetcy and aryl being optionally substituted with 1–3 members selected from $R^a$;
$R^1$ is selected from the group consisting of:
(a) $C_{1-10}$alkyl;
(b) $C_{1-6}$fluoroalkyl, optionally substituted with a hydroxy group;
(c) aryl optionally substituted with 1–3 substituents selected from $R^a$;
(d) heteroaryl, said heteroaryl group being a monocyclic aromatic ring of 5 atoms, said ring having one heteroatom which is O, S or N, and optionally 1, 2, or 3 additional N atoms; or a monocyclic ring of 6 atoms, said ring having one heteroatom which is O, S or N, and optionally 1, 2, or 3 additional N atoms, said heteroaryl group being optionally substituted with from 1–3 substituents selected from $R^a$;
(e) benzoheterocycle in which the heterocycle is a 5, 6, or 7-membered ring containing 1 or 2 heteroatoms selected from O, S and N, optionally containing a carbonyl, sulfinyl or sulfonyl group; said benzoheterocycle being optionally substituted with 1–3 substituents selected from $R^a$;
(f) a heterocycloalkyl group of 5, 6 or 7 members which contains 1 or 2 heteroatoms selected from O, S and N, and optionally containing a carbonyl group or a sulfonyl group;
(g) a benzocarbocycle in which the carbocycle is a 5, 6, or 7-membered ring which optionally contains a carbonyl group, optionally substituted with 1–2 substituents selected from $R^a$;
(h) a bicyclic heteroaryl group having 8, 9 or 10 members, containing 1 to 5 heteroatoms selected from O, S and N, optionally substituted with 1–2 substituents selected from $R^a$; and
(i) hydrogen;
$R^2$ is the acyl residue of an amino acid, the amino group of which may be optionally substituted by $C_{1-6}$ alkyl or an acyl group of the structure $R^1$ZCO—, and in the case of a dicarboxylic amino acid, the terminal carboxyl may optionally be in the form of a $C_{1-4}$alkyl ester;
$R^3$ is selected from the group consisting of:
(a) $C_{1-10}$alkyl,
(b) $C_{1-6}$fluoroalkyl, and
(c) $C_{6-10}$aryl optionally substituted as defined above, and
$R^5$ and $R^6$ independently represent members selected from the group consisting of: H, $C_{1-10}$alkyl, $C_{2-10}$alkenyl, aryl ,Hetcy, $CONH_2$, $CO_2H$, $CO_2$—$R^4$, $C(O)R^4$, $C_{1-6}$fluoroalkyl, aryl, and Hetcy groups being optionally substituted with 1–3 substituents selected from $R^a$;
or $R^5$ and $R^6$ are taken in combination and represent a 7 membered carbocyclic ring, optionally interrupted with 1–3 heteroatoms selected from O, $S(O)y$ and N, and optionally substituted with 1–3 members selected from $R^a$.

2. A compound in accordance with claim 1 wherein $B^{1a}$ represents $CF_2PO_3H_2$.

3. A compound in accordance with claim 1 wherein $B^{2a}$ represents $CF_2CO_2H$.

4. A compound in accordance with claim 1 wherein Y represents $R^1ZC(O)$— or $R^2$.

5. A compound in accordance with claim 4 wherein Y represents $R^1ZC(O)$—, wherein $R^1$ represents
- (c) a mono-, di- or tri-substituted aryl wherein the substituents are selected from the group consisting of
  - (1) hydrogen,
  - (2) halo,
  - (3) $NO_2$,
  - (4) $N_3$,
  - (5) OH,
  - (6) CN,
  - (7) $CONH_2$,
  - (8) $CO_2H$,
  - (9) $CO_2$—$C_{1-10}$alkyl,
  - (10) $C_{1-10}$alkyl,
  - (11) $C_{1-6}$fluoroalkyl,
  - (12) $C_{1-10}$alkoxy,
  - (13) $C_{1-10}$alkylthio,
  - (14) $C_{1-10}$alkylsulfinyl,
  - (15) $C_{1-10}$alkylsulfonyl, or
  - (16) phenyl;
- (d) mono-, di- or tri-substituted heteroaryl wherein the heteroaryl is a monocyclic aromatic ring of 5 atoms, said ring having one heteroatom which is S, O or N, and optionally 1, 2, or 3 additional N atoms; or the heteroaryl is a monocyclic ring of 6 atoms, said ring having one heteroatom which is N, and optionally 1, 2, or 3 additional N atoms, wherein the substituents are selected from the group consisting of
  - (1) hydrogen,
  - (2) halo,
  - (3) $NO_2$,
  - (4) $N_3$,
  - (5) OH,
  - (6) CN,
  - (7) $CONH_2$,
  - (8) $CO_2H$,
  - (9) $CO_2$—$C_{1-10}$alkyl,
  - (10) $C_{1-10}$alkyl,
  - (11) $C_{1-6}$fluoroalkyl,
  - (12) $C_{1-10}$alkoxy,
  - (13) $C_{1-10}$alkylthio,
  - (14) $C_{1-10}$alkylsulfinyl, or
  - (15) $C_{1-10}$alkylsulfonyl;
- (e) a mono- or di- substituted benzoheterocycle in which the heterocycle is a 5, 6, or 7-membered ring which may contain 1 or 2 heteroatoms chosen independently from O, S, or N and which may contain a carbonyl group or a sulfonyl group; wherein the substituents are selected from the group consisting of:
  - (1) hydrogen,
  - (2) halo,
  - (3) $NO_2$,
  - (4) $N_3$,
  - (5) OH,
  - (6) CN,
  - (7) $CONH_2$,
  - (8) $CO_2H$,
  - (9) $CO_2$—$C_{1-10}$alkyl,
  - (10) $C_{1-10}$alkyl,
  - (11) $C_{1-6}$fluoroalkyl,
  - (12) $C_{1-10}$alkoxy,
  - (13) $C_{1-10}$alkylthio,
  - (14) $C_{1-10}$alkylsulfinyl, and
  - (15) $C_{1-10}$alkylsulfonyl;
- (f) a heterocycloalkyl group of 5, 6 or 7 members which contains 1 or 2 heteroatoms chosen from O, S, or N and optionally contains a carbonyl group or a sulfonyl group;
- (g) a mono- or di- substituted benzocarbocycle in which the carbocycle is a 5, 6, or 7-membered ring which optionally contains a carbonyl group, wherein the substituents are selected from the group consisting of
  - (1) hydrogen,
  - (2) halo,
  - (3) $NO_2$,
  - (4) $N_3$,
  - (5) OH,
  - (6) CN,
  - (7) $CONH_2$,
  - (8) $CO_2H$,
  - (9) $CO_2$—$C_{1-10}$alkyl,
  - (10) $C_{1-10}$alkyl,
  - (11) $C_{1-6}$fluoroalkyl,
  - (12) $C_{1-10}$alkoxy,
  - (13) $C_{1-10}$alkylthio,
  - (14) $C_{1-10}$alkylsulfinyl, or
  - (15) $C_{1-10}$alkylsulfonyl;

or (h) a mono- or di-substituted bicyclic heteroaryl of 8, 9, or 10 members, containing 1 to 5 heteroatoms chosen independently from O, S or N, wherein the substituents are selected from the group consisting of
  - (1) hydrogen,
  - (2) halo,
  - (3) $NO_2$,
  - (4) $N_3$,
  - (5) OH,
  - (6) CN,
  - (7) $CONH_2$,
  - (8) $CO_2H$,
  - (9) $CO_2$—$C_{1-10}$alkyl,
  - (10) $C_{1-10}$alkyl,
  - (11) $C_{1-6}$fluoroalkyl,
  - (12) $C_{1-10}$alkoxy,
  - (13) $C_{1-10}$alkylthio,
  - (14) $C_{1-10}$alkylsulfinyl, and
  - (15) $C_{1-10}$alkylsulfonyl.

6. A compound in accordance with claim 1 wherein Y represents $R^1ZC(O)$—, and Z represents $SCH_2$, $SO_2CH_2$ or a bond.

7. A compound in accordance with claim 6 wherein Y represents $R^2$, $R^2$ represents the acyl residue of an amino acid, the amino group of which may be optionally substituted by $C_{1-6}$alkyl or an acyl group of the structure $R^1ZCO$—, and in the case of a dicarboxylic amino acid, the terminal carboxyl may optionally be in the form of a $C_{1-4}$alkyl ester.

8. A compound in accordance with claim 1 of formula Ia:

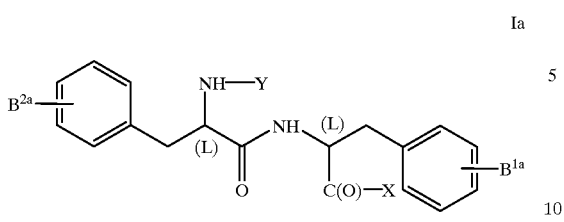

or a pharmaceutically acceptable salt or hydrate thereof.

9. A compound in accordance with claim 1 wherein $R^2$ represents an acyl residue of an amino acid in the L-configuration.

10. A compound in accordance with claim 1 wherein Z is a bond.

11. A compound in accordance with claim 1 wherein X is $NH_2$.

12. A compound in accordance with claim 1 selected from the group consisting of:

(a) (4S)-5-[((1S)-2-[((1S)-2-amino-1-{4-[difluoro(phosphono)methyl]benzyl}-2-oxoethyl)amino]-1-{4-[carboxy(difluoro)methyl]benzyl}-2-oxoethyl)amino]-4-(benzoylamino)-5-oxopentanoic acid;

(b) (4S)-5-[((1S)-2-[((1S)-2-amino-1-{4-[carboxy(difluoro)methyl]benzyl}-2-oxoethyl)amino]-1-{4-[difluoro(phosphono)methyl]benzyl}-2-oxoethyl)amino]-4-(benzoylamino)-5-oxopentanoic acid;

(c) [4-((2S)-3-amino-2-{[(2S)-2-(benzoylamino)-3-(4-hydroxyphenyl)propanoyl]amino}-3-oxopropyl)phenyl](difluoro)methylphosphonic acid, and (d) 2-{4-[(2S)-3-[((1S)-2-amino-1-{4-[difluoro(phosphono)methyl]benzyl}-2-oxoethyl)amino]-2-(benzoylamino)-3-oxopropyl]phenyl}-2,2-difluoroacetic acid.

13. A compound in accordance with one of the following structures:

TABLE 1

|  | Example |
|---|---|
|  | 1 |
|  | 2 |

TABLE 1-continued
| | Example |
|---|---|
| 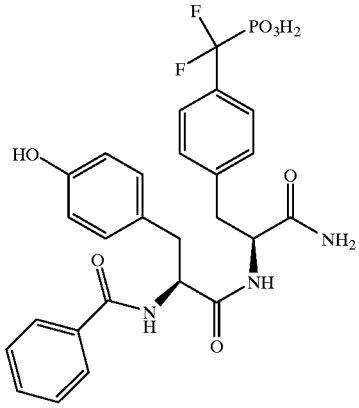 | 3 |
| 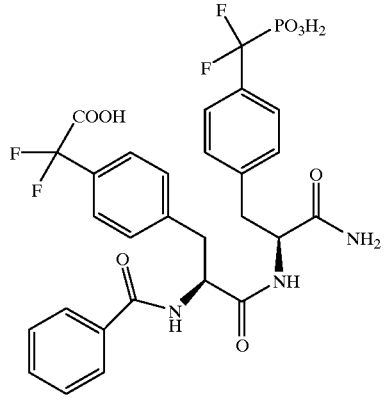 | 4 |
| 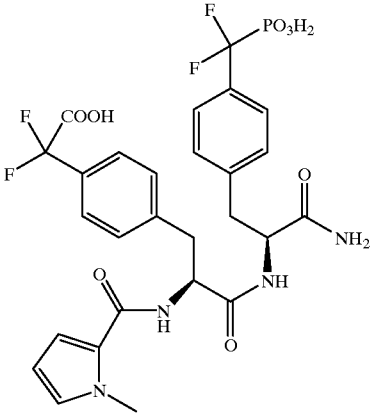 | |

TABLE 1-continued
| Example |
|---|
| 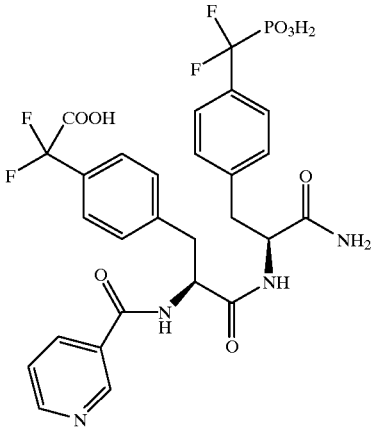 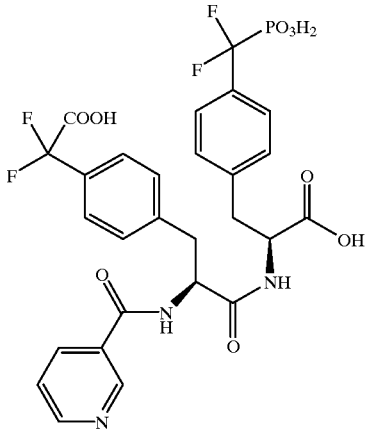 |
| 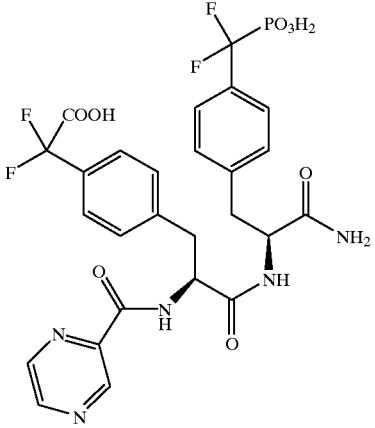 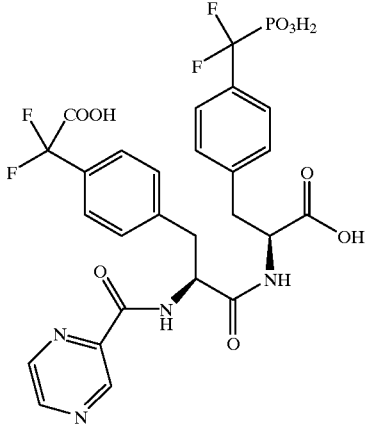 |
| 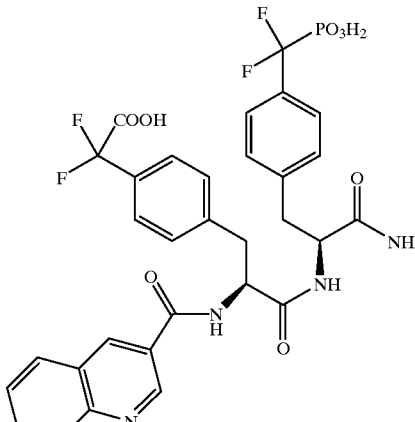 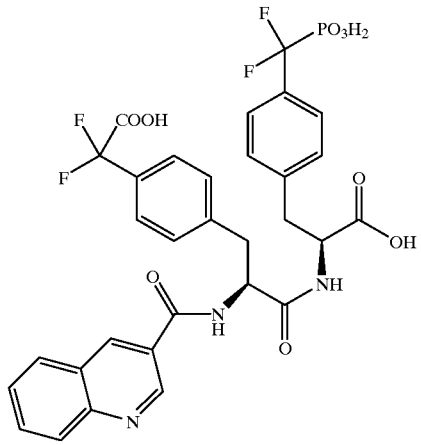 |

TABLE 1-continued
Example
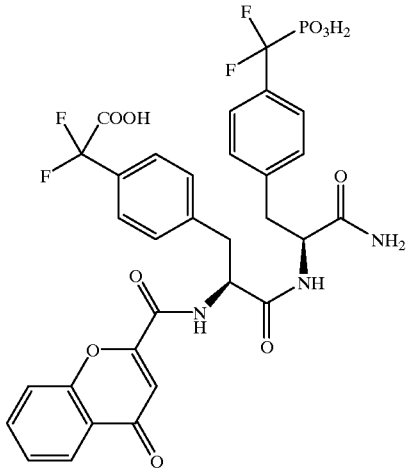
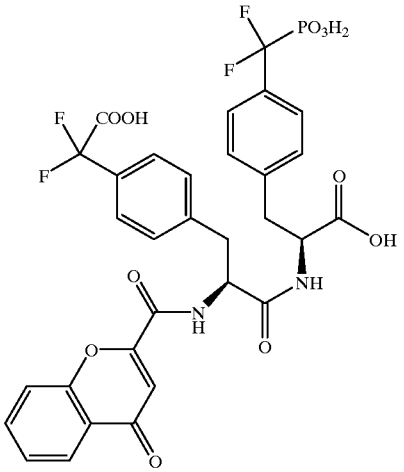
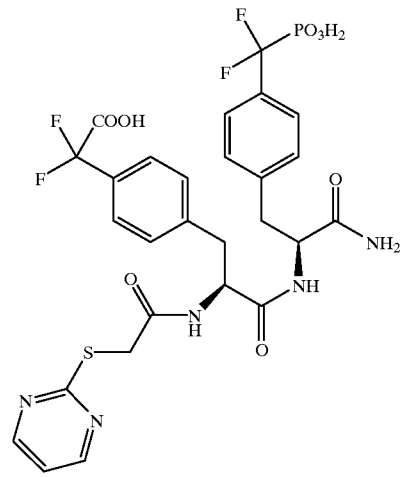
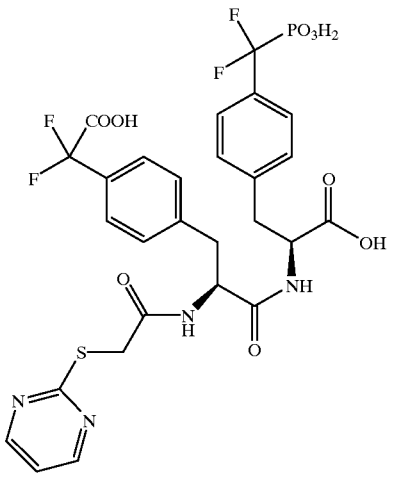
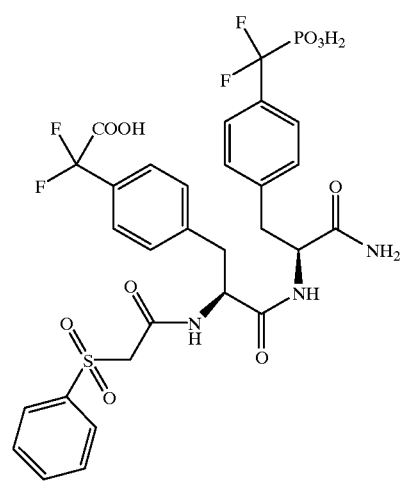
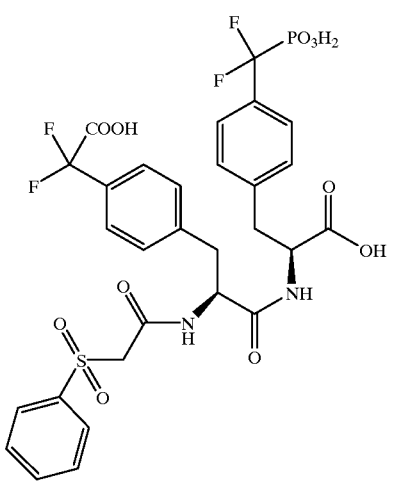

TABLE 1-continued

Example or a pharmaceutically acceptable salt, ester or hydrate thereof.

14. A pharmaceutical composition comprised of a compound in accordance with claim 1 in combination with a pharmaceutically acceptable carrier.

15. A method of treating a PTP-1B mediated disease comprising administering to a patient in need thereof an effective amount of a compound in claim 1, wherein the PTP-1B mediated disease is selected from the group consisting of Type 1 and Type 2 diabetes, glucose intolerance, insulin resistance, and obesity.

* * * * *